United States Patent
Machhammer et al.

(10) Patent No.: US 7,524,987 B2
(45) Date of Patent: *Apr. 28, 2009

(54) PROCESS FOR PREPARING ACROLEIN OR ACRYLIC ACID OR A MIXTURE THEREOF FROM PROPANE

(75) Inventors: Otto Machhammer, Mannheim (DE); Klaus Joachim Müller-Engel, Stutensee (DE); Martin Dieterle, Mannheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

This patent is subject to a terminal disclaimer.

(21) Appl. No.: 11/505,800

(22) Filed: Aug. 18, 2006

(65) Prior Publication Data

US 2007/0117998 A1  May 24, 2007

Related U.S. Application Data

(60) Provisional application No. 60/739,422, filed on Nov. 25, 2005, provisional application No. 60/740,284, filed on Nov. 29, 2005.

(30) Foreign Application Priority Data

Nov. 24, 2005  (DE) .................. 10 2005 056 377
Nov. 29, 2005  (DE) .................. 10 2005 057 197

(51) Int. Cl.
*C07C 51/235* (2006.01)
*C07C 51/16* (2006.01)
*C07C 45/00* (2006.01)

(52) U.S. Cl. .................. 562/532; 562/542; 568/475
(58) Field of Classification Search .................. None
See application file for complete search history.

(56) References Cited

U.S. PATENT DOCUMENTS

| | | | |
|---|---|---|---|
| 3,161,670 A | 12/1964 | Adams et al. | |
| 4,413,147 A | 11/1983 | Khoobiar | |
| 4,532,365 A | 7/1985 | Khoobiar | |
| 4,535,188 A | 8/1985 | Khoobiar | |
| 5,705,684 A * | 1/1998 | Hefner et al. | 562/545 |
| 6,781,017 B2 * | 8/2004 | Machhammer et al. | 568/470 |
| 7,238,827 B2 | 7/2007 | Hechler et al. | |
| 2003/0187299 A1 | 10/2003 | Machhammer et al. | |
| 2004/0063988 A1 | 4/2004 | Hechler et al. | |
| 2004/0181083 A1 | 9/2004 | Proll et al. | |
| 2004/0199001 A1 | 10/2004 | Schindler et al. | |
| 2005/0119515 A1 | 6/2005 | Machhammer et al. | |
| 2006/0004226 A1 | 1/2006 | Machhammer et al. | |
| 2006/0004227 A1 | 1/2006 | Dieterle et al. | |
| 2006/0004229 A1 * | 1/2006 | Dieterle et al. | 562/527 |
| 2006/0258529 A1 | 11/2006 | Diefenbacher et al. | |
| 2007/0088092 A1 | 4/2007 | Klanner et al. | |
| 2007/0123732 A1 * | 5/2007 | Dieterle et al. | 562/545 |

FOREIGN PATENT DOCUMENTS

| | | |
|---|---|---|
| DE | 33 13 573 A1 | 10/1983 |
| DE | 100 28 582 A1 | 12/2001 |
| DE | 102 45 585 A1 | 4/2004 |
| DE | 102 46 119 A1 | 4/2004 |
| DE | 103 16 039 A1 | 10/2004 |
| DE | 10 2004 032 129 A1 | 3/2005 |
| DE | 10 2005 009 885 A1 | 9/2006 |
| DE | 10 2005 009 891 A1 | 9/2006 |
| DE | 10 2005 010 111 A1 | 9/2006 |
| DE | 10 2005 013 039 A1 | 9/2006 |
| DE | 10 2005 022 798 A1 | 11/2006 |
| DE | 10 2005 049 699 A1 | 4/2007 |
| DE | 10 2005 052 923 A1 | 5/2007 |
| EP | 0 117 146 A1 | 8/1984 |
| EP | 0 731 077 A2 | 9/1996 |
| WO | WO 01/96270 A2 | 12/2001 |
| WO | WO 01/96271 A2 | 12/2001 |
| WO | WO 03/011804 A2 | 2/2003 |
| WO | WO 03/076370 A1 | 9/2003 |

* cited by examiner

*Primary Examiner*—Karl J Puttlitz
(74) *Attorney, Agent, or Firm*—Oblon, Spivak, McClelland, Maier & Neustadt, P.C.

(57) ABSTRACT

A process for preparing acrolein, or acrylic acid or a mixture thereof as a target product from propane, in which propane is partially dehydrogenated under heterogeneous catalysis in a reaction zone A, molecular hydrogen thus formed is incinerated partly to water and the product gas A thus formed in reaction zone A is used without secondary component removal to charge a reaction zone B in which propylene present in product gas A is partially oxidized to the target product. From the product gas B formed in reaction zone B, the target product is removed and the residual gas I remaining after an aftertreatment comprising a $CO_2$ scrubbing and a partial discharge thereof is recycled into reaction zone A.

24 Claims, No Drawings

PROCESS FOR PREPARING ACROLEIN OR ACRYLIC ACID OR A MIXTURE THEREOF FROM PROPANE

The present invention relates to a process for preparing acrolein, or acrylic acid or a mixture thereof from propane, in which A)—at least two gaseous feed streams comprising propane, at least one of which comprises fresh propane, are fed to a first reaction zone A to form a reaction gas A, in reaction zone A, reaction gas A is conducted through at least one catalyst bed in which partial heterogeneously catalyzed dehydrogenation of the propane forms molecular hydrogen and propylene, molecular oxygen which oxidizes molecular hydrogen present in reaction gas A in reaction zone A to steam is fed to reaction zone A, and product gas A which comprises molecular hydrogen, steam, propylene and propane is withdrawn from reaction zone A, B) in a reaction zone B, the product gas A withdrawn from reaction zone A, with feeding of molecular oxygen, is used to charge at least one oxidation reactor with a reaction gas B comprising molecular hydrogen, steam, propane, propylene and molecular oxygen, and the propylene present therein is subjected to a heterogeneously catalyzed partial gas phase oxidation to give a product gas B comprising acrolein, or acrylic acid or a mixture thereof as a target product, unconverted propane, molecular hydrogen, steam, carbon dioxide as a by-product, and also other secondary components having lower and higher boiling points than water, C) product gas B is conducted out of reaction zone B, and target product, water and secondary components having a higher boiling point than water present therein are removed therefrom in a first separation zone I to leave a residual gas I which comprises unconverted propane, carbon dioxide, molecular hydrogen, secondary components having a lower boiling point than water and any propylene unconverted in reaction zone B and any unconverted molecular oxygen, D)—as an aftertreatment measure 1, carbon dioxide present in residual gas I is scrubbed out and any water still present in residual gas I is optionally condensed out in a second separation zone II, as an aftertreatment measure 2, a portion of residual gas I is discharged, optionally, as an aftertreatment measure 3, molecular hydrogen present in residual gas I is removed by means of a separating membrane in a third separation zone III and optionally, as an aftertreatment measure 4, any molecular oxygen present in residual gas I is reduced chemically, the sequence of use of aftertreatment measures 1 to 4 being as desired, and E) residual gas I (also referred to as cycle gas I in this document) which comprises unconverted propane and remains after use of aftertreatment measures 1 and 2 and, optionally 3 and/or 4 is recycled into reaction zone A as at least one of the two feed streams comprising propane.

Acrylic acid is an important commodity chemical which finds use, inter alia, as a monomer for preparing polymers which are used as binders, for example in disperse distribution in aqueous medium. A further field of use of acrylic acid polymers is that of superabsorbents in the hygiene sector and other fields of application.

Acrolein is an important intermediate, for example for the preparation of glutaraldehyde, methionine, 1,3-propanediol, 3-picoline, folic acid and acrylic acid.

The process described in the preamble of this document for preparing acrolein, or acrylic acid or a mixture thereof from propane is known in a similar manner (cf., for example, DE-A 33 13 573 and EP-A 117 146).

It differs from the similar processes described in the documents DE-A 10 2004 032 129, EP-A 731 077, DE-A 10 2005 049 699, DE-A 10 2005 052 923, WO 01/96271, WO 03/011804, WO 03/076370, WO 01/96270, DE-A 10 2005 009 891, DE-A 10 2005 013 039, DE-A 10 2005 022 798, DE-A 10 2005 009 885, DE-A 10 2005 010 111, DE-A 102 45 585, DE-A 103 16 039, WO 03/011804 especially in that no substance removal is undertaken on the product gas A withdrawn from reaction zone A before it is used to charge reaction zone B. This is advantageous in that product of value and energy losses and also apparatus demands normally accompanying such substance removals (especially in the case of thermal separation processes) are avoided at this point. However, even the process according to the preamble of this document is not entirely capable of avoiding such substance removals. Instead, like all cycle gas processes, it requires not just at least one target product outlet but also at least one secondary component outlet. However, the process described at the outset of this document is attractive in that it moves the secondary component removal into the vicinity of the target product removal and hence to the point where substance and thermal gradients with a high level of energy and apparatus demands would necessarily have to be enforced in any case in order to reach the goal. A coupling of the secondary component removal to such expenditures reduces the overall level of energy and apparatus demands.

An individually prominent secondary component in the relevant cycle gas process is the molecular hydrogen formed in reaction zone A.

In contrast to the exothermic heterogeneously catalyzed oxydehydrogenation, which is forced by oxygen present and in which free hydrogen is neither formed as an intermediate (the hydrogen pulled from the hydrocarbon to be hydrogenated is pulled out directly as water ($H_2O$)) nor is detectable, the heterogeneously catalyzed dehydrogenation to be carried out in reaction zone A is understood to mean a ("conventional") dehydrogenation, is endothermic (an exothermic hydrogen combustion may be included in reaction zone A as a subsequent step) and in which free molecular hydrogen is formed at least as an intermediate. This generally requires different reaction conditions and different catalysts to the oxydehydrogenation.

In other words, the relevant process proceeds in reaction zone A necessarily with evolution of $H_2$. Since the molecular hydrogen evolved in reaction zone A in this way is not a reactant in the literal sense in the target reaction proceeding in reaction zone B, it is not naturally consumed in the relevant cycle gas process. It is thus for the operator to determine where and in what form the molecular hydrogen formed in reaction zone A (and also any added to reaction zone A) should be discharged again in the cycle gas process described (in the ideal case, one hydrogen molecule is formed per propylene molecule formed in reaction zone A).

A proposal made in the documents of the closest prior art (cf. for example, U.S. Pat. No. 3,161,670, EP-A 117 146, DE-A 33 13 573) consists in operating reaction zone A with exclusion of molecular oxygen and conducting the molecular hydrogen formed additionally in its entirety as inert gas up to beyond separation zone I and then combusting it with the molecular oxygen unconverted in reaction zone B under heterogeneous catalysis fully to water and recycling the water formed in its entirety into reaction zone A and hence not removing the molecular hydrogen formed in reaction zone A until the second pass through the circuit and exclusively in separation zone I in its oxidized form, specifically as water. Such a procedure is disadvantageous in several ways. Firstly, molecular hydrogen which has not been removed burdens reaction gas B with a potentially explosive constituent which has both specific diffusion behavior (certain construction materials are permeable to molecular hydrogen) and a marked reduction potential (in-house investigations have shown that presence of increased amounts of molecular hydrogen in reaction gas B have an adverse effect on the lifetime of the catalysts to be used for the heterogeneously catalyzed partial gas oxidation), and, secondly, the target product has to be removed from a not inconsiderable amount of water in separation zone I, which is associated with a significant energy requirement, since the target products have a high affinity for water (increased amounts of water in reaction gas B generally equally reduce the lifetime of the catalysts used for the partial oxidation, generally comprising Mo in oxidic form, since $H_2O$ promotes the sublimation of Mo oxides). In addition, in the case of the hydrogen combustion described, an extremely high heat of combustion is released at a point beyond separation zone I, the extent of which is difficult to utilize locally in an advantageous manner. Inseparably associated with the above-described problems is the use of an excess of molecular oxygen relative to the target reaction stoichiometry, which is advantageous for an increased catalyst lifetime in the partial oxidation of reaction zone B but naturally implies increased explosion risks in reaction zone B (when acrylic acid is the target product and the entire amount of molecular oxygen required is added beforehand to reaction gas B, a molar ratio of molecular oxygen present in reaction gas B to propylene present therein of at least >1.5 is required (this already takes into account minor full combustion of propylene)).

As an alternative, the prior art cited also offers a process variant in which the entire amount of molecular hydrogen formed in reaction zone A is likewise conducted initially as such up to beyond separation zone I. It is then recommended to remove the entire amount of propane and propylene present in residual gas I from all other constituents of residual gas I, including the molecular hydrogen, and only to recycle the stream of $C_3$ hydrocarbons thus separated into reaction zone A in an insulated manner. However, a disadvantage of this procedure is that it is associated with the need to first fully convert the entire amount of $C_3$ hydrocarbons to the condensed phase and then to recycle it therefrom back into the gas phase.

As a further proposal, DE-A 33 13 573 comprises the possibility of oxidizing the molecular hydrogen formed in reaction zone A fully to water by means of added molecular oxygen in reaction zone A, and of either condensing out at least a portion of the water formed upstream of reaction zone B and removing it in this way, or to conduct it additionally in the entire amount formed into reaction zone B. Both are disadvantageous. Firstly, condensing-out of water entails cooling of product gas A to temperatures which are well below the temperatures required in reaction zone B.

Secondly, this temperature reduction has to be effected starting from a very high temperature level, since combustion of molecular hydrogen affords about twice the amount of heat which is consumed for its formation in the dehydrogenation.

Moreover, leaving the entire amount of water obtained in the reaction gas in separation zone I results in an increased level of separation complexity as already described, and generally in a shortened catalyst lifetime in reaction zone B.

In view of the prior art described, it was an object of the present invention to provide a process in accordance with the preamble of the present document which has the disadvantages described at worst in reduced form.

The comparatively simple solution to the stated object consists in spreading both the discharge of the molecular hydrogen formed in reaction zone A and the generation of the discharge form over a relatively large zone of the process. While observing the pre-requisite of undertaking the discharge exclusively beyond reaction zone B and advantageously (only) implementing partial discharge in separation zone I in the form of water generated beforehand in reaction zone A by hydrogen combustion, water of partial oxidation formed inevitably in reaction zone B is removed additionally in any case in separation zone I in the known processes for target product removal, so that separation zone I already naturally comprises appropriate separating equipment.

Accordingly, the solution found to the inventive object is a process for preparing acrolein, or acrylic acid or a mixture thereof from propane, in which A)—at least two gaseous feed streams comprising propane, at least one of which comprises fresh propane, are fed to a first reaction zone A to form a reaction gas A in reaction zone A, reaction gas A is conducted through at least one catalyst bed in which partial heterogeneously catalyzed dehydrogenation of the propane forms molecular hydrogen and propylene, molecular oxygen which oxidizes molecular hydrogen present in reaction gas A in reaction zone A to steam is fed to reaction zone A, and product gas A which comprises molecular hydrogen, steam, propylene and propane is withdrawn from reaction zone A, B) in a reaction zone B, the product gas A withdrawn from reaction zone A, with feeding of molecular oxygen, is used to charge at least one oxidation reactor with a reaction gas B comprising molecular hydrogen, steam, propane, propylene and molecular oxygen, and the propylene present therein is subjected to a heterogeneously catalyzed partial gas phase oxidation to give a product gas B comprising acrolein, or acrylic acid or a mixture thereof as a target product, unconverted propane, molecular hydrogen, steam, carbon dioxide as a by-product, and also other secondary components having lower and higher boiling points than water, C) product gas B is conducted out of reaction zone B, and target product, water and secondary components having a higher boiling point than water present therein are removed therefrom in a first separation zone I to leave a residual gas I which comprises unconverted propane, carbon dioxide, molecular hydrogen, secondary components having a lower boiling point than water and any propylene unconverted in reaction zone B and any unconverted molecular oxygen, D)—as an aftertreatment measure 1, carbon dioxide present in residual gas I is scrubbed out and any water still present in residual gas I is optionally condensed out in a second separation zone II, as an aftertreatment measure 2, a portion of residual gas I is discharged, optionally, as an aftertreatment measure 3, molecular hydrogen present in residual gas I is removed by means of a separating membrane in a third separation zone III and optionally, as an aftertreatment measure 4, any molecular oxygen present in residual gas I is reduced chemically, the sequence of use of aftertreatment measures 1 to 4 being as desired, and E) aftertreated residual gas I (also referred to as cycle gas I in this document) which comprises unconverted propane and remains after use of aftertreatment measures 1 and 2 and, optionally 3 and/or 4 is recycled into reaction zone A as at least one of the two feed streams comprising propane, wherein an amount M of molecular hydrogen which is at least 5 mol % but not more than 95 mol % of the total amount of molecular hydrogen produced in reaction zone A and, optionally, fed to reaction zone A is oxidized to steam in reaction zone A.

Preferably in accordance with the invention, the amount M (always on a corresponding basis) is at least 10 mol % but not more than 90 mol %. More preferably, the amount M is at least 15 mol % but not more than 85 mol %. Even better, the amount M is at least 20 mol % but not more than 80 mol %. Even more preferably, the amount M is at least 25 mol % but not more than 75 mol %. Even better, the amount M is at least 30 mol % and at most 70 mol %. Also advantageous is an amount M of at least 35 mol % and at most 65 mol %. Even better, the amount M is at least 40 mol % but not more than 60 mol %. At best, the amount M is at least 45 mol % and not more than 55 mol %. M=50 mol % is very particularly advantageous in accordance with the invention.

An important advantage of the inventive procedure is that propane, in the course of its entire circulation, remains predominantly in the gaseous state of matter, i.e. does not have to be converted to the condensed, liquid phase. This is advantageous not least because propane is a comparatively nonpolar molecule whose condensation is comparatively costly and inconvenient.

Another advantageous characteristic of the process according to the invention is that reaction gas B necessarily comprises molecular hydrogen in an amount restricted in accordance with the invention. This is because it possesses, in addition to the disadvantageous properties already mentioned in relation to the teaching of DE-A 33 13 573 and of EP-A 117 146, also the advantageous property that it behaves chemically inertly in reaction zone B. In other words, at least 95 mol %, usually even at least 97 mol % or at least 99 mol % of the molecular hydrogen fed to reaction zone B remains chemically unchanged as it passes through reaction zone B.

However, it simultaneously has the advantage of the highest thermal conductivity among the gases. According to Walter J. Moore, Physikalische Chemie [Physical Chemistry], WDEG Verlag, Berlin (1973), page 171, the thermal conductivity under standard conditions is, for example, more than ten times as large as the thermal conductivity of carbon dioxide and about eight times as large as that of molecular nitrogen or molecular oxygen.

It is this increased thermal conductivity which, according to table I of DE-A 33 13 573, appears to be responsible for the selectivity of COx formation in the presence of molecular hydrogen being significantly lower in reaction zone B than in the absence of molecular hydrogen. Owing to more rapid heat transport from the location of reaction in reaction zone B, it causes relatively low catalyst surface temperatures and accordingly a lower proportion of propylene full combustion. This is especially true when, as in the process according to the invention, highly thermally conductive molecular hydrogen and highly thermally absorbing propane are involved together in a synergistic manner in transporting heat away.

In this document, fresh propane is understood to mean propane which has not yet taken part in a dehydrogenation in reaction zone A. In general, it is fed as a constituent of crude propane (which preferably fulfills the specification according to DE-A 102 46 119 and DE-A 102 45 585) which also comprises small amounts of components other than propane. Such crude propane is obtainable, for example, by the process described in DE-A 10 2005 022 798. In general, only residual gas I aftertreated in accordance with the invention is fed as a further propane-comprising feed stream in addition to fresh propane to reaction zone A.

In the process according to the invention, preference is given to feeding fresh propane exclusively into reaction zone A, as a constituent of the charge gas mixture for reaction zone A. In principle, it is also possible for portions of the fresh propane, for reasons of explosion safety, also to be fed into the charge gas mixtures of the first and/or second oxidation stage of reaction zone B.

Reaction gas B, with which reaction zone B is charged, in this document appropriately equally satisfies the specification recommended in DE-A 102 46 119 and DE-A 102 45 585. In addition, appropriately in accordance with the invention, a mechanical separating operation according to DE-A 103 16 039 is connected between reaction zone A and reaction zone B.

The loading of a catalyst bed catalyzing a reaction step with reaction gas is understood in this document to mean the amount of reaction gas in standard liters (=l(STP); the volume in liters that the corresponding amount of reaction gas would take up under standard conditions (0° C., 1 bar) which is conducted through one liter of catalyst bed (for example fixed catalyst bed) per hour.

It is also possible for the loading to be based only on one constituent of the reaction gas. In that case, it is the amount of this constituent in l(STP)/l·h, which is conducted through one liter of the catalyst bed per hour (pure inert material beds are not included in the fixed catalyst bed). When the catalyst bed consists of a mixture of catalyst and inert shaped bodies, the loading, when it is mentioned correspondingly, may also be based only on the volume unit of catalyst present.

In this document, an inert gas is generally understood to mean a reaction gas constituent which behaves substantially chemically inertly under the conditions of the appropriate reaction and, each inert reaction gas constituent taken on its own, remains chemically unchanged to an extent of more than 95 mol %, preferably to an extent of more than 97 mol % or to an extent of more than 99 mol %.

Typical reaction gases B with which reaction zone B can be charged in the process according to the invention have the following contents:

from 4 to 25% by volume of propylene,
from 6 to 70% by volume of propane,
from 5 to 60% by volume of $H_2O$,
from 8 to 65% by volume of $O_2$ and
from 0.3 to 20% by volume of $H_2$.

Reaction gases B preferred in accordance with the invention have the following contents:

from 6 to 15% by volume of propylene,
from 6 to 60% by volume of propane,
from 5 to 30% by volume of $H_2O$,
from 8 to 35% by volume of $O_2$ and
from 2 to 18% by volume of $H_2$.

Reaction gases B very particularly preferred in accordance with the invention for the aforementioned charge have the following contents:

from 8 to 14% by volume of propylene, from 20 to 55% by volume, preferably from 20 to 45% by volume of propylene, from 10 to 25% by volume of $H_2O$, from 10 to 25% by volume, preferably from 15 to 20% by volume of $O_2$ and from 6 to 15% by volume of $H_2$.

The advantage of moderate propane contents in reaction gas B is evident, for example, from DE-A 102 45 585.

Within the aforementioned composition framework, it is favorable when the molar ratio $V_1$ of propane present in reaction gas B to propylene present in reaction gas B is from 1 to 9 (i.e., advantageously in accordance with the invention, a propane/propene separation according to WO 04/094041 can be dispensed with). In addition, it is advantageous within the aforementioned composition framework when the ratio $V_2$ of molecular oxygen present in reaction gas B to propylene present in reaction gas B is from 1 to 2.5. It is also advantageous in the context of the present invention within the aforementioned composition framework when the ratio $V_3$ of propylene present in reaction gas B to molecular hydrogen present in reaction gas B is from 0.5 to 20. It is also advantageous within the aforementioned composition framework when the molar ratio $V_4$ of steam present in reaction gas B to the total molar amount of propane and propylene present in reaction gas B is from 0.005 to 10.

Particularly advantageously, $V_1$ in the reaction gas B used to charge reaction zone B (in reaction gas B starting mixture) is from 1 to 7 or to 4, or from 2 to 6, and particularly favorably from 2 to 5, or from 3.5 to 4.5. It is also preferred for reaction gas B starting mixture when $V_2$ is from 1.2 to 2.0, or from 1.4 to 1.8. It is also advantageous for reaction gas B starting mixture when $V_3$ is from 0.5 to 15, or from 0.5 to 10, or from 0.5 to 1.5. Correspondingly, $V_4$ in reaction gas B starting mixture is preferably from 0.01 to 5, better from 0.05 to 3, advantageously from 0.1 to 1 and more advantageously from 0.1 to 0.5 or else 0.3.

Preference is given in accordance with the invention to nonexplosive reaction gas B starting mixtures.

A crucial factor in answering the question of whether reaction gas B starting mixture is explosive or not is whether combustion (ignition, explosion) initiated by a local ignition source (for example glowing platinum wire) spreads under certain conditions (pressure, temperature) or not (cf. DIN 51649 and the investigation description in WO 04/007405). When there is spreading, the mixture shall be designated here as explosive. When there is no spreading, the mixture is classified in this document as nonexplosive. When the starting reaction gas mixture of an inventive partial oxidation is nonexplosive, this also applies to reaction gas mixtures formed therefrom in the course of the partial oxidation (cf. WO 04/007405).

The source used for (the) molecular oxygen which is required at reaction zone B but is not present in product gas A may be molecular oxygen as such, or a mixture of molecular oxygen and a gas which behaves chemically inertly in reaction zone B (for example noble gases such as argon, molecular nitrogen, steam, carbon dioxide, etc.) (or a mixture of such inert gases) (for example air). Preferably in accordance with the invention, the molecular oxygen is supplied as a gas which comprises not more than 30% by volume, preferably not more than 25% by volume, advantageously not more than 20% by volume, more advantageously not more than 15% by volume, better not more than 10% by volume and more preferably not more than 5% by volume of other gases (other than molecular oxygen). It is particularly favorable when the molecular oxygen to be supplied to reaction zone B is fed thereto in its pure form.

The aforementioned applies in principle in the same manner to the molecular oxygen to be fed to reaction zone A in the process according to the invention over and above the molecular oxygen present, if appropriate, in the aftertreated residual gas I recycled into reaction zone A. However, since the oxygen demand in reaction zone A is comparatively low, it is also favorable to use air as the oxygen source for the oxygen demand in reaction zone A in the process according to the invention, especially for reasons of economic viability.

The aftertreated residual gas l recycled into reaction zone A in the process according to the invention will generally still comprise molecular oxygen remaining in reaction zone B and this oxygen content of the aftertreated residual gas l recycled into reaction zone A may in principle even be such that it does not require any further feeding of molecular oxygen into reaction zone A over and above this. However, the aftertreated residual gas l recycled into reaction zone A, in accordance with the invention, need not necessarily be oxygen-comprising and, in many cases in accordance with the invention, an additional oxygen feed is required in reaction zone A. This can then be done in the form of pure oxygen or in the form of a mixture of molecular oxygen and one or more gases which behave chemically inertly in reaction zones A, B (for example $N_2$, $H_2O$, noble gases and/or $CO_2$) (for example in the form of air). Preferably in accordance with the invention, it is effected in the form of gas which comprises not more than 30% by volume, preferably not more than 25% by volume, advantageously not more than 20% by volume, more advantageously not more than 15% by volume, better not more than 10% by volume and more preferably not more than 5% by volume or not more than 2% by volume of other gases other than molecular oxygen. It is particularly advantageous at this point too to feed pure oxygen.

The above-described feed of pure oxygen preferred in accordance with the invention both into reaction zone A and into reaction B is especially advantageous because it does not burden the circulation process according to the invention with inert gas which has to be discharged again in the further course of the circulation process over and above that which is unavoidable.

Quite generally, it is typical for the process according to the invention that the total amount in the reaction gas B starting mixture of constituents other than propylene, molecular hydrogen, steam, propane and molecular oxygen is usually $\leq 40\%$ by volume, or $\leq 35\%$ by volume, or $\leq 30\%$ by volume, or $\leq 25\%$ by volume, or $\leq 20\%$ by volume, in many cases $\leq 15\%$ by volume, frequently $\leq 10\%$ by volume. Such total contents of $\leq 5\%$ by volume can be realized only with difficulty in the context of the inventive procedure. Of these other constituents of the reaction gas B starting mixture, up to 80% by volume may be ethane and/or methane. Otherwise, such contents will in particular be carbon oxides ($CO_2$, CO) and noble gas, but also secondary component oxygenates such as formaldehyde, benzaldehyde, methacrolein, acetic acid, propionic acid, methacrylic acid, etc. It will be appreciated that ethylene, isobutene, n-butane, n-butenes and molecular nitrogen are also included in these possible other constituents of the reaction gas B starting mixture. However, one fundamental advantage (cf. EP-A 293 224) of the inventive procedure is that the reaction gas B starting mixture may comprise from 0.1 to 30% by volume or 1 to 25 or 20% by volume, in many cases from 5 to 15% by volume of $CO_2$. The CO content will normally be $\leq 5\%$ by volume, or $\leq 4\%$ by volume, or $\leq 3\%$ by volume, or $\leq 2\%$ by volume, usually $\leq 1\%$ by volume. However, it typically comprises ≦20% by volume, preferably ≦15% by volume, more preferably ≦10% by volume and most preferably ≦5% by volume of $N_2$.

In principle, useful in reaction zone A are all known heterogeneously catalyzed partial dehydrogenations of propane, as known, for example, from the documents WO 03/076370, WO 01/96271, EP-A 117 146, WO 03/011804, EP-A 731 077, U.S. Pat. No. 3,161,670, WO 01/96270, DE-A 33 13 573, DE-A 102 45 585, DE-A 103 16 039, DE-A 10 2005 009 891, DE-A 10 2005 013 039, DE-A 10 2005 022 798, DE-A 10 2005 009 885, DE-A 10 2005 010 111, DE-A 10 2005 049 699, and also from the German application DE-A 10 2004 032 129.

In other words, based on single pass of the propane fed to reaction zone A through reaction zone A, reaction zone A can be configured isothermally by virtue of controlled heat exchange with fluid (i.e. liquid or gaseous) heat carriers conducted outside reaction zone A. However, with the same reference basis, it can also be designed adiabatically, i.e. substantially without such a controlled heat exchange with heat carriers conducted outside reaction zone A. In the latter case, the gross thermal character, based on single pass of the propane fed to reaction zone A through reaction zone A, by taking measures which have been recommended in the above documents and are still to be described below, may be configured endothermically (negative) or autothermally (substantially zero) or exothermically (positive). It is equally possible to employ the catalysts recommended in the aforementioned documents in the process according to the invention. In principle, the heterogeneously catalyzed propane dehydrogenation, irrespective of whether it is operated adiabatically or isothermally, can be carried out either in a fixed bed reactor or in a moving bed or fluidized bed reactor (owing to its backmixing, the latter is suitable especially for heating of reaction gas mixture A starting mixture to the reaction temperature in reaction zone A by hydrogen combustion in reaction gas A when cycle gas I comprises molecular oxygen).

Typically, the heterogeneously catalyzed partial dehydrogenation of propane to propylene requires comparatively high reaction temperatures. The achievable conversion is normally restricted by the thermodynamic equilibrium. Typical reaction temperatures are from 300 to 800° C. or from 400 to 700° C. One molecule of hydrogen is obtained per molecule of propane dehydrogenated to propylene. The working pressure in reaction zone A is typically from 0.3 to 5 or 3 bar. Preferably in accordance with the invention, the working pressure in reaction zone A is from 2 to 5 bar, or to 4 bar. However, it may also be up to 20 bar. When reaction zone A is operated at very high pressures (e.g. from >5 or 10 to 20 bar) and at least an amount of hydrogen which corresponds to at least 50% of the total amount of the molecular hydrogen produced in reaction zone A is combusted therein, it is advantageous to decompress product gas A by expansion in an expansion turbine, and to use the work performed additionally to drive the compressor for the residual gas I prior to its $CO_2$ scrubbing. At the same time, product gas A cools to a temperature required for further use in reaction zone B. High temperatures and removal of the $H_2$ reaction product shift the equilibrium position toward the target product in reaction zone A.

Since the heterogeneously catalyzed dehydrogenation reaction proceeds with increasing volume, the conversion can be increased by lowering the partial pressure of the dehydrogenation products. This can be achieved in a simple manner, for example, by dehydrogenating at reduced pressure (however, performance at elevated pressure is generally advantageous for the catalyst lifetime) and/or by adding substantially inert diluent gases, for example steam which normally constitutes an inert gas for the dehydrogenation reaction. As a further advantage, dilution with steam generally causes reduced carbonization of the catalyst used, since the steam reacts with carbon formed by the principle of coal gasification. The heat capacity of steam is also capable of balancing out part of the endothermicity of the dehydrogenation.

While steam in limited amounts is normally found to be beneficial for the activity of the partial oxidation catalysts in the downstream reaction zone B, an amount over and above this is disadvantageous in reaction zone B for the reasons already mentioned. According to the invention, a portion of hydrogen additionally has to be oxidized to steam in reaction zone A. It is therefore advantageous in accordance with the invention when the amount of steam fed to reaction zone A, based on the reaction gas A fed to the catalyst charge of reaction zone A, is ≦20% by volume, preferably ≦15% by volume and more preferably ≦10% by volume. In general, the amount of steam fed to reaction zone A, on the same basis, will normally, however, be ≧1% by volume, in many cases ≧2% by volume, or ≧3% by volume and frequently ≧5% by volume.

Further diluents suitable for the heterogeneously catalyzed propane dehydrogenation are, for example, nitrogen, noble gases such as He, Ne and Ar, but also compounds such as CO, $CO_2$, methane and ethane. All diluents mentioned may be used additionally either alone or in the form of different mixtures. When the aforementioned diluent gases are formed as a by-product in the cycle gas process according to the invention or are fed as fresh gas (or fresh gas constituent), a discharge in an appropriate amount is required in the process according to the invention, which is why a corresponding fresh gas feed is of low preference in accordance with the invention. However, it is possible in principle in the process according to the invention to circulate a substantially constant amount of a diluent gas and to replace attendant losses with fresh gas.

In principle, useful dehydrogenation catalysts for the heterogeneously catalyzed propane dehydrogenation are all of those known in the prior art. They can be divided roughly into two groups, specifically into those which are of oxidic nature (for example chromium oxide and/or aluminum oxide) and into those which consist of at least one generally comparatively noble metal (for example platinum) on a generally oxidic support. The dehydrogenation catalysts which may be used thus include all of those recommended in WO 01/96270, EP-A 731077, DE-A 10211275, DE-A 10131297, WO 99/46039, U.S. Pat. No. 4,788,371, EP-A-0 705 136, WO 99/29420, U.S. Pat. No. 4,220,091, U.S. Pat. No. 5,430,220, U.S. Pat. No. 5,877,369, EP-A-0 117 146, DE-A 199 37 196, DE-A 199 37 105 and DE-A 199 37 107. In particular, the catalyst according to example 1, example 2, example 3 and example 4 of DE-A 199 37 107 may be used.

These are dehydrogenation catalysts which comprise from 10 to 99.9% by weight of zirconium dioxide, from 0 to 60% by weight of aluminum oxide, silicone dioxide and/or titanium dioxide and from 0.1 to 10% by weight of at least one element of the first or second main group, of an element of the third transition group, of an element of the eighth transition group of the Periodic Table of the Elements, lanthanum and/or tin, with the proviso that the sum of the percentages by weight add up to 100% by weight.

Also particularly suitable is the dehydrogenation catalyst used in the working example of this document.

Generally, the dehydrogenation catalysts may be catalyst extrudates (diameter typically from 1 to 10 mm, preferably from 1.5 to 5 mm; length typically from 1 to 20 mm, preferably from 3 to 10 mm), tablets (preferably the same dimensions as for the extrudates) and/or catalysts rings (external diameter and length in each case typically from 2 to 30 nm or to 1.0 mm, wall thickness appropriately from 1 to 10 mm, or to 5 mm, or to 3 mm). To carry out the heterogeneously catalyzed dehydrogenation in a fluidized bed or moving bed, more finely divided catalysts will accordingly be used. Preference is given in accordance with the invention to a fixed catalyst bed for reaction zone A.

In general, the dehydrogenation catalysts (especially those used by way of example in this document and those recommended in DE-A 199 37 107 (especially the exemplary catalysts of this DE-A)) are such that they are capable of catalyzing both the dehydrogenation of propane and the combustion of molecular hydrogen. The combustion of hydrogen proceeds very much more rapidly over the catalysts in comparison to the dehydrogenation of propane in the case of a competition situation.

For the performance of the heterogeneously catalyzed propane dehydrogenation, useful reactor types and process variants are in principle all of those known in the prior art. Descriptions of such process variants are present, for example, in all prior art documents cited with regard to the dehydrogenation catalysts and the prior art cited at the outset of this document.

A comparatively comprehensive description of dehydrogenation processes suitable in accordance with the invention is also present in Catalytica® Studies Division, Oxidative Dehydrogenation and Alternative Dehydrogenation Processes, Study Number 4192 OD, 1993, 430 Ferguson Drive, Mountain View, Calif., 94043-5272 U.S.A.

As already stated, it is characteristic of the partial heterogeneously catalyzed dehydrogenation of propane that it precedes endothermically. This means that the heat (energy) required for the attainment of the required reaction temperature and that required for the reaction has to be supplied to reaction gas A either beforehand and/or in the course of the heterogeneously catalyzed dehydrogenation. If appropriate, reaction gas A has to withdraw the heat of reaction required from itself.

In addition, owing to the high reaction temperatures required, it is typical of heterogeneously catalyzed dehydrogenations of propane that small amounts of high molecular weight organic compounds having a high boiling point, up to and including carbon, are formed and are deposited on the catalyst surface, thus deactivating it. In order to minimize this disadvantageous accompanying phenomenon, the propane-containing reaction gas A which is to be passed at elevated temperature over the catalyst surface for the heterogeneously catalyzed dehydrogenation, can, as already discussed, be diluted with steam. Carbon which is deposited is eliminated partly or fully under the conditions given in this way by the principle of coal gasification.

Another means of removing deposited carbon compounds consists in allowing a gas comprising oxygen (appropriately in the absence of hydrocarbons) to flow through the dehydrogenation catalyst from time to time at elevated temperature and thus effectively burning off the deposited carbon. However, a certain suppression of the formation of carbon deposits is also possible by adding molecular hydrogen to the propane to be dehydrogenated under heterogeneous catalysis before it is conducted over the dehydrogenation catalyst at elevated temperature.

It will be appreciated that the possibility also exists of adding a mixture of steam and molecular hydrogen to the propane to be dehydrogenated under heterogeneous catalysis. Addition of molecular hydrogen to the heterogeneously catalyzed dehydrogenation of propane also reduces the undesired formation of allene (propadiene), propyne and acetylene as by-products.

Thus, it is possible in the simplest case to feed only fresh propane and cycle gas I to reaction zone A to form a reaction gas A to be conducted through the at least one catalyst bed (also referred to in this document as charge gas mixture of reaction zone A or reaction gas A starting mixture). The cycle gas I may already comprise the amount of molecular oxygen which is required in order to cause the combustion of hydrogen which is required in accordance with the invention in reaction zone A. This is because molecular oxygen is preferably used in excess in reaction zone B relative to the reaction stoichiometry and normally remains substantially in the cycle gas I in the process according to the invention.

In the case described above, the cycle gas I will also regularly comprise just enough steam that it can develop its advantageous properties for the overall process together with the steam formed in the combustion of hydrogen in reaction zone A. In the case described above, there is no need to feed further gaseous streams into the reaction zone A. The reaction desired in reaction zone A proceeds in single pass of reaction gas A through reaction zone A.

It will be appreciated that it is also possible to feed in steam and/or molecular hydrogen in addition to fresh propane and cycle gas I to form the reaction gas A to be conducted through the at least one catalyst bed, in order to develop the advantageous action of steam and molecular hydrogen described in this document. The molar ratio of molecular hydrogen to propane in the charge gas mixture of reaction zone A is generally $\leq 5$. The molar ratio of steam to propane in the charge gas mixture of reaction zone A may, for example, be from $\geq 0$ to 30, appropriately from 0.1 to 2 and favorably from 0.5 to 1. It is also possible if required to feed extra molecular hydrogen (in pure form and/or as a mixture with inert gas) and/or extra inert gas to the charge gas mixture for reaction zone A. The reaction desired in reaction zone A can then be effected again in single pass of reaction gas A (of the charge gas of reaction zone A) through reaction zone A without further gaseous streams being fed in along the reaction path. In this document, the reaction path in reaction zone A shall be understood to mean the flow path of that propane which is fed to reaction gas A before its first pass through at least one catalyst bed of reaction zone A through reaction zone A as a function of the dehydrogenating conversion (the conversion in the heterogeneously catalyzed dehydrogenation) of this propane.

A suitable reactor form for such a heterogeneously catalyzed propane dehydrogenation with single pass of the charge gas mixture through reaction zone A and without intermediate gas feeding is, for example, the fixed bed tubular reactor or tube bundle reactor. In this reactor, the dehydrogenation catalyst is disposed in one reaction tube or in a bundle of reaction tubes as a fixed bed. When the combustion of hydrogen required in accordance with the invention in reaction zone A is such that the gross reaction proceeding in reaction zone A proceeds endothermically, the reaction tubes will appropriately be heated from outside in accordance with the invention (it will be appreciated that they may also be cooled if required). This can be effected, for example, by combusting a gas, for example a hydrocarbon such as methane, in the space surrounding the reaction tubes. It is favorable to apply this direct form of catalyst tube heating only to the first 20 to 30% of the fixed bed and to heat the remaining bed length to the required reaction temperature through the radiative heat released in the course of combustion. In this way, an approximately isothermal reaction is achievable. Suitable reaction tube internal diameters are from about 10 to 15 cm. A typical dehydrogenation tube bundle reactor comprises from 300 to 1000 or more reaction tubes. The temperature in the reaction tube interior typically varies within the range from 300 to 700° C., preferably within the range from 400 to 700° C. Advantageously, reaction gas A starting mixture is fed to the tubular reactor preheated to the reaction temperature. It is possible that product gas (mixture) A leaves the reaction tube with a temperature lower by 50 to 100° C. However, this outlet temperature may also be higher or at the same level. In the aforementioned procedure, the use of oxidic dehydrogenation catalysts based on chromium oxide and/or aluminum oxide is appropriate. The dehydrogenation catalyst is usually employed undiluted. On the industrial scale, a plurality of such tube bundle reactors can be operated in parallel and their product gases A used in a mixture to charge reaction zone B. If appropriate, it is also possible for only two of these reactors to be in dehydrogenation operation, while the catalyst charge is regenerated in the third reactor.

A single pass of the charge gas through reaction zone A can also be effected in a moving bed or fluidized bed reactor, as described, for example, in DE-A 102 45 585 and the literature cited on this subject in this document.

In principle, reaction zone A of the process according to the invention may also consist of two sections. Such a construction of reaction zone A is advisable especially when the charge gas for reaction zone A does not comprise any molecular oxygen (this may be the case, for example, when cycle gas I does not comprise any molecular oxygen).

In this case, the actual heterogeneously catalyzed dehydrogenation can be effected in the first section and, after an intermediate supply of molecular oxygen and/or a mixture of molecular oxygen and inert gas, the heterogeneously catalyzed combustion of hydrogen required in accordance with the invention can be effected in the second section.

Quite generally, reaction zone A in the process according to the invention will appropriately be operated in such a way that, based on a single pass through reaction zone A, from $\geq 5$ mol % to $\leq 60$ mol %, preferably from $\geq 10$ mol % to $\leq 50$ mol %, more preferably from $\geq 15$ mol % to $\leq 40$ mol %, and most preferably from $\geq 20$ mol % to $\leq 35$ mol % of the total amount of propane fed to reaction zone A are converted in a dehydrogenating manner in reaction zone A. Such a restricted conversion in reaction zone A is normally sufficient in accordance with the invention because the remaining amount of unconverted propane functions substantially as a diluent gas in the downstream reaction zone B and, in the further course of the inventive procedure, can be recycled substantially without loss into reaction zone A. The advantage of a procedure with low propane conversion is that, on single pass of reaction gas A through reaction zone A, the amount of heat required for the endothermic dehydrogenation is comparatively low and comparatively low reaction temperatures are sufficient to achieve the conversion.

Advantageously in accordance with the invention, it may, as already addressed, be appropriate to carry out the propane dehydrogenation in reaction zone A (quasi-)adiabatically (for example with comparatively low propane conversion). This means that the charge gas mixture for reaction zone A will generally first be heated to a temperature of from 500 to 700° C. (or from 550 to 650° C.) (for example by direct firing of the surrounding wall). Normally, a single adiabatic pass through a catalyst bed will then be sufficient in order to achieve both the desired dehydrogenating conversion and the combustion of hydrogen required in accordance with the invention, in the course of which the reaction gas, depending on the quantitative ratio of endothermic dehydrogenation and exothermic combustion of hydrogen will be heated, be cooled or behave in a thermally neutral manner in the gross evaluation. Preference is given in accordance with the invention to an adiabatic operating mode in which the reaction gas cools by from about 30 to 200° C. in single pass. If required, in a second section of reaction zone A, hydrogen formed in the dehydrogenation can be postcombusted under heterogeneous catalysis with intermediately fed molecular oxygen. This combustion can equally be carried out adiabatically.

Remarkably, especially in adiabatic operation, a single shaft furnace reactor which is flowed through axially and/or radially by reaction gas A is sufficient as a fixed bed reactor.

In the simplest case, this is a single closed reaction volume, for example a vessel, whose internal diameter is from 0.1 to 10 m, possibly even from 0.5 to 5 m, and in which the fixed catalyst bed is placed on a support device (for example a grid). The reaction volume which has been charged with catalyst and is substantially heat-insulated in adiabatic operation is flowed through axially by the hot reaction gas A comprising propane. The catalyst geometry may be either spherical or annular or extrudate-shaped. Since the reaction volume can be realized in this case by a very inexpensive apparatus, all catalyst geometries which have a particularly low pressure drop are preferable. These are in particular catalyst geometries which lead to a large cavity volume or are in structured form, for example monoliths or honeycombs. To realize radial flow of reaction gas A comprising propane, the reactor may, for example, consist of two concentric cylindrical grids disposed in a shell and the catalyst bed may be arranged in their annular gap. In the adiabatic case, the metal shell would in turn be thermally insulated if appropriate.

Suitable inventive catalyst charges for a heterogeneously catalyzed propane dehydrogenation are especially also the catalysts disclosed in DE-A 199 37 107, in particular all of those disclosed by way of example, and mixtures thereof with geometric shaped bodies inert with respect to the heterogeneously catalyzed dehydrogenation.

After a prolonged operating time, the aforementioned catalysts can be regenerated in a simple manner by, at an inlet temperature of from 300 to 600° C., frequently from 400 to 550° C., initially passing air (preferably) diluted with nitrogen and/or steam over the catalyst bed in first regeneration stages. The catalyst (bed) loading with regeneration gas (e.g. air) may, for example, be from 50 to 10000 $h^{-1}$ and the oxygen content of the regeneration gas may be from 0.1 or 0.5 to 20% by volume.

In subsequent further regeneration stages, it is possible to use air as the regeneration gas under otherwise identical regeneration conditions. Appropriately from application point of view, it is recommended to flush the catalyst with inert gas (for example $N_2$) before it is regenerated.

Subsequently, it is generally advisable to regenerate with pure molecular hydrogen or with molecular hydrogen diluted with inert gas (preferably steam and/or nitrogen) (the hydrogen content should be $\geq 1$% by volume) under otherwise identical conditions.

The heterogeneously catalyzed propane dehydrogenation in reaction zone. A of the process according to the invention can be operated with comparatively low propane conversion ($\leq 30$ mol %) in all cases at the same catalyst (bed) loadings (relating both to the reaction gas overall and to propane present therein) as the variants with high propane conversion (>30 mol %). These loadings with reaction gas A may, for example, be from 100 to 40000 or to 10000 $h^{-1}$, frequently from 300 to 7000 $h^{-1}$, i.e. in many cases from about 500 to 4000 $h^{-1}$.

In a particularly elegant manner, the heterogeneously catalyzed propane dehydrogenation in reaction zone A (especially in the case of propane conversions of from 15 to 35 mol % based on single pass) can be implemented in a tray reactor.

This reactor comprises more than one catalyst bed catalyzing the dehydrogenation in spatial succession. The catalyst bed number may be from 1 to 20, appropriately from 2 to 8, but also from 3 to 6. Increased propane conversions can be achieved increasingly readily with increasing number of trays. The catalyst beds are preferably arranged in radial or axial succession. Appropriately from an application point of view, the fixed catalyst bed type is used in such a tray reactor.

In the simplest case, the fixed catalyst beds in a shaft furnace reactor are arranged axially or in the annular gaps of concentric cylindrical grids. However, it is also possible to arrange the annular gaps in segments one above another and to conduct the gas, after it has passed radially through one segment, into the next segment above it or below it.

Appropriately, reaction gas A is subjected to intermediate heating on its way from one catalyst bed to the next catalyst bed, for example by passing it over heat exchanger surfaces (e.g. ribs) heated with hot gases or by passing it through pipes heated with hot combustion gases (if required, it is also possible to effect intermediate cooling in a corresponding manner).

When the tray reactor is otherwise operated adiabatically, it is sufficient especially for propane conversions of $\leq 30$ mol %, in particular when using the catalysts described in DE-A 199 37 107, especially those of the exemplary embodiments, to conduct the reaction gas mixture into the dehydrogenation reactor preheated to a temperature of from 450 to 550° C. (preferably from 450 to 500° C.) and to keep it in this temperature range within the tray reactor. This means that the entire propane dehydrogenation can thus be realized at extremely low temperatures, which is found to be particularly favorable for the lifetime of the fixed catalyst beds between two regenerations. For higher propane conversions, the reaction gas mixture is appropriately conducted into the dehydrogenation reactor preheated to higher temperatures (these may be up to 700° C.) and kept in this elevated temperature range within the tray reactor.

It is even more elegant to carry out the above-outlined intermediate heating in a direct way (enables an autothermal method). To this end, a limited amount of molecular oxygen is added to reaction gas A either before it flows through the first catalyst bed (for example as a constituent of cycle gas I) (in that case, reaction gas A starting mixture should advantageously comprise added molecular hydrogen) and/or between the downstream catalyst beds. It is thus possible (generally catalyzed by the dehydrogenation catalysts themselves) to bring about the limited combustion, required in accordance with the invention, of molecular hydrogen which is present in reaction gas A, has been formed in the course of the heterogeneously catalyzed propane dehydrogenation and/ or has been added to reaction gas A in a particularly selective and controlled manner (it may also be appropriate from an application point of view to insert catalyst beds in the tray reactor which are charged with catalyst which particularly specifically (selectively) catalyzes the combustion of hydrogen (examples of useful such catalysts include those of the documents U.S. Pat. No. 4,788,371, U.S. Pat. No. 4,886,928, U.S. Pat. No. 5,430,209, U.S. Pat. No. 5,530,171, U.S. Pat. No. 5,527,979 and U.S. Pat. No. 5,563,314; for example, such catalyst beds may be accommodated in the tray reactor in alternation to the beds comprising dehydrogenation catalyst; these catalysts are also suitable for the above-described hydrogen combustion in a second section of reaction zone A)). Depending on the amount of molecular hydrogen combusted, the heat of reaction released thus allows an exothermic operating mode overall, or an autothermal operating mode overall (the gross thermal character is substantially zero), or an endothermic operating mode overall for the heterogeneously catalyzed propane dehydrogenation. As the selected residence time of the reaction gas in the catalyst bed increases, propane dehydrogenation is thus possible at decreasing or substantially constant temperature, which enables particularly long lifetimes between two regenerations and is preferred in accordance with the invention.

Generally, oxygen feeding as described above should be undertaken in accordance with the invention in such a way that the oxygen content of reaction gas A, based on the amount of molecular hydrogen present therein, is from 0.5 to 50 or to 30% by volume, preferably from 10 to 25% by volume. Useful oxygen sources include both pure molecular oxygen (preferred in accordance with the invention) or molecular oxygen diluted with inert gas, for example CO, $CO_2$, $N_2$ and/or noble gases, but especially also air. Preferably in accordance with the invention, the molecular oxygen is fed in as gas which comprises not more than 30% by volume, preferably not more than 25% by volume, advantageously not more than 20% by volume, more advantageously not more than 15% by volume, better not more than 10% by volume and more preferably not more than 5% by volume of other gases (other than molecular oxygen). Particularly advantageously, the oxygen feeding described is effected in pure form.

Since the combustion of 1 mol of molecular hydrogen to $H_2O$ affords about twice as much energy (approx. 240 kJ/mol) as the dehydrogenation of 1 mol of propane to propylene and $H_2$ (approx. 120 kJ/mol), an autothermal configuration of reaction zone A in an adiabatic tray reactor as described is particularly appropriate to the aim with regard to the contemplated advantage of the inventive procedure, in that it entails merely the combustion of an amount of hydrogen of about 50 mol % of the amount of molecular hydrogen formed in the dehydrogenation in reaction zone A.

However, the advantage of the process according to the invention does not only come into effect when an amount of hydrogen of about 50 mol % of the amount of molecular hydrogen formed in reaction zone A is combusted in reaction zone A. Instead, this advantage comes into effect even when an amount of hydrogen of from 5 to 95 mol %, preferably from 10 to 90 mol %, more preferably from 15 to 85 mol %, even more preferably from 20 to 80 mol %, even better from 25 to 75 mot %, more favorably from 30 to 70 mol %, even more advantageously from 35 to 65 mol % and most advantageously from 40 to 60 mol % or from 45 to 55 mol % of the amount of molecular hydrogen formed in reaction zone A is combusted to give water (preferably in the above-described operating mode of an adiabatic tray reactor).

In general, feeding of oxygen as described above should be undertaken such that the oxygen content of reaction gas A, based on the amount of propane and propylene pre-sent therein, is from 0.01 or 0.5 to 3% by volume.

The isothermicity of the heterogeneously catalyzed propane dehydrogenation can be improved further by incorporating closed (for example tubular) internals which have favorably, but not necessarily, been evacuated before filling in the spaces between the catalyst beds in the tray reactor. Such internals may also be placed into the particular catalyst bed. These internals comprise suitable solids or liquids which evaporate or melt above a certain temperature and consume heat as they do so, and, when the temperature falls below this value, condense again and release heat as they do so.

Another means of heating the charge gas mixture for the heterogeneously catalyzed propane dehydrogenation in reaction zone A to the required reaction temperature consists in combusting a portion of the propane and/or $H_2$ present therein by means of molecular oxygen present in the charge gas mixture on entry into reaction zone A (for example over suitable specific combustion catalysts, for example by simply passing it through and/or passing it over) and, by means of the heat of combustion thus released, bringing about the heating to the reaction temperature desired for the dehydrogenation (such a procedure is (as already mentioned) advantageous especially in a fluidized bed reactor).

In accordance with the above, reaction zone A of the process according to the invention can be configured as described in the documents DE-A 10 2004 032 129 and DE-A 10 2005 013 39, but with the difference that the charge gas mixture of reaction zone A used is a mixture of steam, fresh propane and cycle gas I. Reaction zone A is implemented as a (preferably adiabatic) tray reactor in which catalyst beds (preferably fixed beds) are arranged in radial or axial succession. Advantageously, the number of catalyst bed trays in such a tray reactor is three. Preference is given to carrying out the heterogeneously catalyzed partial propane dehydrogenation autothermally. To this end, a limited amount of molecular oxygen or such a mixture comprising it with inert gas is added to the charge gas mixture of reaction zone A beyond the first (fixed) catalyst bed passed through and between the (fixed) catalyst beds downstream of the first (fixed) catalyst bed in flow direction. Thus, generally catalyzed by the dehydrogenation catalysts themselves, limited combustion of hydrogen formed in the course of the heterogeneously catalyzed propane dehydrogenation (and, if appropriate, of propane and propylene to a minor extent at most) is brought about, whose exothermic thermal character substantially maintains the dehydrogenation temperature.

Appropriately, the partial heterogeneously catalyzed dehydrogenation of propane is essentially operated distributed over the three catalyst trays such that the conversion of the propane conducted into the reactor, based on single reactor pass, is approx. 20 mol % (it will be appreciated that it may also be 30 mol %, or 40 mol %, or 50 mol % in the process according to the invention). The selectivity of propylene formation achieved is regularly 90 mol %. The maximum contribution of a single tray to the conversion migrates from the front backward in flow direction with increasing operating time. In general, the catalyst charge is regenerated before the third tray in flow direction provides the maximum contribution to the conversion. Advantageously, the regeneration is effected when the carbonization of all trays has attained an identical extent.

It is quite generally favorable for the above-described heterogeneously catalyzed partial dehydrogenation of propane when the loading on the total amount of catalyst (sum over all beds) with the total amount of propane and propylene is $\geq 500$ l (STP)/l·h and $\leq 20000$ l (STP)/l·h (typical values are from 1500 l (STP)/l·h to 2500 l (STP)/l·h). The maximum reaction temperature within an individual fixed catalyst bed is advantageously kept at from 500° C. to 600° C. (or to 650° C.). Particularly advantageously, the charge gas mixture for reaction zone A in the above-described heterogeneously catalyzed propane dehydrogenation in the tray reactor consists merely of fresh propane and the cycle gas l which has been recycled from the partial oxidation into the dehydrogenation and, stemming from the partial oxidation, generally comprises a sufficient amount of steam to result in a satisfactory lifetime of the dehydrogenation catalyst beds.

A disadvantage of the above-described process is that virtually all catalysts which catalyze the dehydrogenation of propane also catalyze the combustion (full oxidation) of propane and propylene to carbon oxides and steam) of propane and propylene with molecular oxygen, and, as already stated, molecular oxygen is normally present in the cycle gas l from the partial oxidation which is recycled into the heterogeneously catalyzed partial dehydrogenation of propane.

According to DE-A 102 11 275, this can be counteracted by dividing the product gas withdrawn from the dehydrogenation zone into two portions of identical composition in order to feed only one of the two portions to the partial oxidation as product gas A, while the other portion is recycled into the dehydrogenation as a constituent of reaction gas A. The molecular hydrogen present in this cycle gas II coming from the dehydrogenation itself is then intended to protect the propane and, if appropriate, propylene present in the charge gas mixture for reaction zone A from the molecular oxygen which is likewise present therein. This protection is based on the fact that the combustion, normally catalyzed heterogeneously by the same catalysts, of molecular hydrogen to water is preferred kinetically over the full combustion of propane and/or propylene.

Following the teaching of DE-A 102 11 275, the dehydrogenation gas circulation will appropriately be realized by the jet pump principle (it is also referred to as loop mode). This document also addresses the possibility of adding molecular hydrogen additionally to the charge gas mixture for reaction zone A as further oxidation protection. DE-A 10 2005 049 699 makes an appropriate statement on the requirement to meter the molecular hydrogen into the motive jet for the pump in a certain feed hierarchy.

According to the teaching of DE-A 10 2004 032 129 and DE-A 10 2005 013 039, the recycling of a cycle gas I which comprises molecular oxygen and stems from the heterogeneously catalyzed partial oxidation will advantageously not be undertaken into the charge gas mixture for the heterogeneously catalyzed partial propane dehydrogenation. Instead, this recycling into reaction gas A of reaction zone A will not be effected until after a certain dehydrogenation conversion. DE-A 10 2004 032 129 also proposes adding external molecular hydrogen preferably additionally to the charge gas mixture of reaction zone A prior to this recycling. In addition, DE-A 10 2004 032 129 also propagates the loop mode for the dehydrogenation. In this case, applied to the inventive procedure, motive jet is exclusively the cycle gas I recycled from the partial oxidation into the dehydrogenation.

Following the teaching of working example 11 of DE-A 10 2005 009 885, a loop mode in which the charge gas mixture for the inventive reaction zone A is composed of cycle gas I, of fresh propane, of external molecular hydrogen, of a minimum amount of external steam and of cycle gas II recycled from the dehydrogenation itself (it would then also be possible to dispense with the external steam) will preferably be employed therein. The motive jet used is a mixture of fresh propane, external molecular hydrogen, cycle gas I from the partial oxidation and external steam. With regard to the metering sequence to be observed advantageously in the generation of the motive jet, DE-A 10 2005 049 699 gives an advantageous recommendation.

Advantageously in accordance with the invention, cycle gas I generally comprises not only molecular oxygen and steam but also molecular hydrogen, carbon monoxide and carbon dioxide. In other words, it generally also comprises CO. Preferably in accordance with the invention, cycle gas I comprises from 5 to 15% by volume of $CO_2$.

Advantageously in accordance with the invention, the product gas A withdrawn from reaction zone A in the process according to the invention has the following contents:

| | |
|---|---|
| Propane | from 25 to 60% by volume, |
| Propene | from 8 to 25% by volume, |
| $H_2$ | from 0.04 to 25% by volume, frequently to 15% by volume, |
| $H_2O$ | from 2 to 25% by volume and |
| $CO_2$ | from >0 to 30% by volume, frequently to 15% by volume. |

The temperature of product gas A is typically from 400 to 700° C., preferably from 450 to 650° C.

The pressure of the product gas A leaving reaction zone A is, preferably in accordance with the invention, from 2 to 4 bar. However, it may also, as already mentioned, be up to 20 bar.

According to the invention, product gas A, without any further secondary component removal, is then used to charge the at least one oxidation reactor in reaction zone B with reaction gas B.

Advantageously, it is sufficient for this purpose to add to product gas A that amount of molecular oxygen which is required for the attainment of the objective in reaction zone B. This addition may in principle be effected as pure oxygen or as a mixture (e.g. air) of molecular oxygen and one or more gases which behave chemically inertly in reaction zone B (for example $N_2$, $H_2O$, noble gases, $CO_2$). Preferably in accordance with the invention, it is effected as a gas which comprises not more than 30% by volume, preferably not more than 25% by volume, advantageously not more than 20% by volume, more advantageously not more than 15% by volume, better not more than 10% by volume and more preferably not more than 5% by volume or not more than 2% by volume of other gases other than molecular oxygen. Very particularly advantageous at this point is the use of pure oxygen. Normally, the amount of molecular oxygen fed in will be such that the molar ratio of molecular oxygen present to propane present in the charge gas for reaction zone B (in the reaction gas B starting mixture) is $\geq 1$ and $\leq 3$. Before the molecular oxygen is fed into product gas A, product gas A is cooled, appropriately in accordance with the invention, to a temperature in the range from 250 to 350° C., preferably in the range from 270 to 320° C. Advantageously in accordance with the invention, this cooling is brought about by indirect heat exchange (preferably in countercurrent operation; this statement applies quite generally to indirect heat exchange in this document, unless explicitly stated otherwise). The coolant used is preferably the reaction gas A starting mixture for reaction zone A which is simultaneously brought to the reaction temperature desired in reaction zone A (in principle, the cooling can also be effected, as already mentioned, by decompressing in an expansion turbine when the starting pressure is sufficiently high in this regard).

In a skillful manner in accordance with the invention, the feeding of gas comprising molecular oxygen to the product gas A preferably cooled as described above can be accomplished such that product gas A is used as a motive jet to operate a jet pump which comprises a motive nozzle, a mixing zone, a diffuser and a suction nozzle, the conveying direction of the motive jet decompressed through the motive nozzle via the mixing zone and the diffuser pointing into the inlet of the at least one oxidation reactor in reaction zone B, and the suction action of the suction nozzle pointing in the direction of the source of the gas comprising molecular oxygen and the gas comprising the molecular oxygen being sucked in by the reduced pressure generated in the suction nozzle and transported through the mixing zone via the diffuser with simultaneous mixing with the motive jet, and the reaction gas B starting mixture formed being released into the inlet of the second reaction zone B, or into the inlet of the at least one oxidation reactor of the second reaction zone B. The aforementioned variant can be employed especially when product gas A has a pressure of from 2 to 5 bar or more, or to 4 bar.

It will be appreciated that the gas comprising molecular oxygen can also be mixed in a conventional manner with product gas A to give the charge gas mixture for reaction zone B (reaction gas B starting mixture). Appropriately in accordance with the invention, a mechanical separating operation according to DE-A 103 16 039 can be connected between reaction zone A and reaction zone B.

In a manner known per se, the heterogeneously catalyzed gas phase partial oxidation of propylene to acrylic acid with molecular oxygen proceeds in principle in two steps successive along the reaction coordinate, of which the first leads to acrolein, and the second from acrolein to acrylic acid.

This reaction sequence in two steps successive in time opens up the possibility in a manner known per se of terminating the process according to the invention in reaction zone B at the stage of acrolein (the stage of predominant acrolein formation) and undertaking the target product removal at this stage, or continuing the process according to the invention up to predominant acrylic acid formation and only then undertaking the target product removal.

When the process according to the invention is carried out up to predominant acrylic acid formation, it is advantageous in accordance with the invention to perform the process in two stages, i.e. in two oxidation stages arranged in series, in which case the fixed catalyst bed to be used and preferably also the other reaction conditions, for example the temperature of the fixed catalyst bed, are appropriately adjusted in an optimizing manner in each of the two oxidation stages.

Although the multimetal oxides comprising the elements Mo, Fe, Bi which are particularly suitable as active compositions for the catalysts of the first oxidation stage (propylene→acrolein) are also capable to a certain extent of catalyzing the second oxidation stage (acrolein→acrylic acid), preference is normally given for the second oxidation stage to catalysts whose active composition is at least one multimetal oxide comprising the elements Mo and V.

The process, to be carried out in reaction zone B in accordance with the invention, for the heterogeneously catalyzed partial oxidation of propylene over fixed catalyst beds whose catalysts have, as an active composition, at least one multimetal oxide comprising the elements Mo, Fe and Bi is thus suitable in particular as a one-stage process for preparing acrolein (and acrylic acid if appropriate) or as the first reaction stage for the two-stage preparation of acrylic acid.

The realization of the one-stage heterogeneously catalyzed partial oxidation of propylene to acrolein and acrylic acid if appropriate or the two-stage heterogeneously catalyzed partial oxidation of propylene to acrylic acid using a reaction gas B obtained in accordance with the invention may specifically be carried out as described in the documents EP-A 70 07 14 (first reaction stage; as described there, but also in corresponding countercurrent mode of salt bath and starting reaction gas mixture over the tube bundle reactor), EP-A 70 08 93 (second reaction stage; as described there, but also in corresponding countercurrent mode), WO 04/085369 (especially this document is regarded as being an integral part of this document) (as a two-stage process), WO 04/85363, DE-A 103 13 212 (first reaction stage), EP-A 1 159 248 (as a two-stage process), EP-A 1 159 246 (second reaction stage), EP-A 1 159 247 (as a two-stage process), DE-A 199 48 248 (as a two-stage process), DE-A 101 01 695 (one-stage or two-stage), WO 04/085368 (as a two-stage process), DE 10 2004 021 764 (two-stage), WO 04/085362 (first reaction stage), WO 04/085370 (second reaction stage), WO 04/085365 (second reaction stage), WO 04/085367 (two-stage), EP-A 990 636, EP-A 1 007 007 and EP-A 1 106 598.

This is especially true of all working examples contained in these documents. They may be carried out as described in these documents, but with the difference that the starting reaction gas mixture used for the first reaction stage (propylene to acrolein) is a reaction gas B generated in accordance with the invention. Regarding the remaining parameters, the procedure is as in the working examples of the documents mentioned (especially regarding the fixed catalyst beds and reactant loading of the fixed catalyst beds). When the procedure in the aforementioned working examples of the prior art is in two stages and there is secondary oxygen feeding (secondary air feeding in a manner less preferred in accordance with the invention) between the two reaction stages, the feeding is undertaken in an appropriate manner, but is adjusted in its amount to the effect that the molar ratio of molecular oxygen to acrolein in the charge gas mixture of the second reaction stage corresponds to that in the working examples of the documents mentioned.

Advantageously in accordance with the invention, the amounts of oxygen in reaction zone B are such that product gas B still comprises unconverted molecular oxygen (appropriately from ≧0.5 to 6% by volume, advantageously from 1 to 5% by volume, preferably from 2 to 4% by volume). In the case of a two-stage procedure, the aforementioned applies to each of the two oxidation stages.

Multimetal oxide catalysts particularly suitable for the particular reaction stage have been described many times before and are well known to those skilled in the art. For example, EP-A 253 409 refers on page 5 to corresponding US patents.

Favorable catalysts for the particular oxidation stage are also disclosed by DE-A 44 31 957, DE-A 10 2004 025 445 and DE-A 44 31 949. This is especially true of those of the general formula I in the two aforementioned documents. Particularly advantageous catalysts for the particular oxidation stage are disclosed by the documents DE-A 103 25 488, DE-A 103 25 487, DE-A 103 53 954, DE-A 103 44 149, DE-A 103 51 269, DE-A 103 50 812 and DE-A 103 50 822.

For the inventive reaction stage for the heterogeneously catalyzed gas phase partial oxidation of propylene to acrolein or acrylic acid or a mixture thereof, useful multimetal oxide compositions are in principle all multimetal oxide compositions comprising Mo, Bi and Fe as the active composition.

These are in particular the multimetal oxide active compositions of the general formula I of DE-A 199 55 176, the multimetal oxide active compositions of the general formula I of DE-A 199 48 523, the multimetal oxide active compositions of the general formulae I, II and III of DE-A 101 01 695, the multimetal oxide active compositions of the general formulae I, II and III of DE-A 199 48 248 and the multimetal oxide active compositions of the general formulae I, II and III of DE-A 199 55 168 and also the multimetal oxide active compositions specified in EP-A 700 714.

Also suitable for this reaction stage are the multimetal oxide catalysts comprising Mo, Bi and Fe which are disclosed in the documents Research Disclosure No. 497012 of 08.29.2005, DE-A 100 46 957, DE-A 100 63 162, DE-C 3 338 380, DE-A 199 02 562, EP-A 15 565, DE-C 2 380 765, EP-A 8 074 65, EP-A 27 93 74, DE-A 330 00 44, EP-A 575897, U.S. Pat. No. 4,438,217, DE-A 19855913, WO 98/24746, DE-A 197 46 210 (those of the general formula II), JP-A 911294239, EP-A 293 224 and EP-A 700 714. This applies in particular to the exemplary embodiments in these documents, and among these particular preference is given to those of EP-A 15 565, EP-A 575 897, DE-A 197 46 210 and DE-A 198 55 913. Particular emphasis is given in this context to a catalyst according to example 1c from EP-A 15 565 and also to a catalyst to be prepared in a corresponding manner but whose active composition has the composition $Mo_{12}Ni_{6.5}Zn_2Fe_2Bi_1P_{0.0065}K_{0.06}O_x \cdot 10\ SiO_2$. Emphasis is also given to the example having the serial number 3 from DE-A 198 55 913 (stoichiometry: $Mo_{12}CO_7Fe_3Bi_{0.6}K_{0.08}Si_{1.6}O_x$) as an unsupported hollow cylinder catalyst of geometry 5 mm×3 mm×2 mm (external diameter×height×internal diameter) and also to the unsupported multimetal oxide II catalyst according to example 1 of DE-A 197 46 210. Mention should also be made of the multimetal oxide catalysts of U.S. Pat. No. 4,438,217. The latter is especially true when these hollow cylinders have a geometry of 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Further possible catalyst geometries in this context are extrudates (for example length 7.7 mm and diameter 7 mm; or length 6.4 mm and diameter 5.7 mm).

A multitude of the multimetal oxide active compositions suitable for the step from propylene to acrolein and, if appropriate, acrylic acid can be encompassed by the general formula IV

$$Mo_{12}Bi_aFe_bX^1_cX^2_dX^3_eX^4_fO_n \qquad (IV)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in IV other than oxygen.

They are obtainable in a manner known per se (see, for example, DE-A 4 023 239) and are customarily shaped in substance to give spheres, rings or cylinders or else used in the form of coated catalysts, i.e. preshaped inert support bodies coated with the active composition. They may of course also be used as catalysts in powder form (for example in the fluidized bed reactors).

In principle, active compositions of the general formula IV can be prepared in a simple manner by obtaining a very intimate, preferably finely divided dry mixture having a composition corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature. Useful sources for the elemental constituents of the multimetal oxide active compositions IV are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture).

The starting compounds for preparing multimetal oxide active compositions IV can be intimately mixed in dry or in wet form. When they are mixed in dry form, the starting compounds are appropriately used as finely divided powders and subjected to calcination after mixing and optional compacting. However, preference is given to intimate mixing in wet form. Typically, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The multimetal oxide active compositions of the general formula IV may be used for the "propylene→acrolein (and acrylic acid if appropriate)" step either in powder form or shaped to certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Instead of graphite, it is also possible to use hexagonal boron nitride as an assistant in the shaping, as recommended by DE-A 10 2005 037 678. Examples of suitable unsupported catalyst geometries include solid cylinders or hollow cylinders having an external diameter and a length of from 2 to 10 mm. In the case of the hollow cylinder, a wall thickness of from 1 to 3 mm is advantageous. The unsupported catalyst can of course also have spherical geometry, and the spherical diameter can be from 2 to 10 mm.

A particularly favorable hollow cylinder geometry is 5 mm×3 mm×2 mm (external diameter×length×internal diameter), especially in the case of unsupported catalysts.

The pulverulent active composition or its pulverulent precursor composition which is yet to be calcined and/or partially calcined may of course also be shaped by applying to preshaped inert catalyst supports. The coating of the support bodies to produce the coated catalysts is generally performed in a suitable rotatable vessel, as disclosed, for example, by DE-A 29 09 671, EP-A 293 859 or EP-A 714 700. To coat the support bodies, the powder composition to be applied is appropriately moistened and dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are the customary porous or nonporous aluminum oxides, silicon dioxide, thorium dioxide, zirconium dioxide, silicon carbide or silicates such as magnesium silicate or aluminum silicate. They generally behave substantially inertly with regard to the target reaction on which the process according to the invention is based. The support bodies can have a regular or irregular shape, although preference is given to regularly shaped support bodies having distinct surface roughness, for example spheres or hollow cylinders. Suitable support bodies are substantially nonporous, surface-roughened spherical supports made of steatite whose diameter is from 1 to 10 mm or to 8 mm, preferably from 4 to 5 mm. However, suitable support bodies are also cylinders whose length is from 2 to 10 mm and whose external diameter is from 4 to 10 mm. In the case of rings suitable in accordance with the invention as support bodies, the wall thickness is also typically from 1 to 4 mm. Annular support bodies to be used with preference in accordance with the invention have a length of from 2 to 6 mm, an external diameter of from 4 to 8 mm and a wall thickness of from 1 to 2 mm. Support bodies suitable in accordance with the invention are in particular also rings of geometry 7 mm×3 mm×4 mm (external diameter×length×internal diameter). The fineness of the catalytically active oxide compositions to be applied to the surface of the support body is of course adjusted to the desired coating thickness (cf. EP-A 714 700).

Multimetal oxide active compositions to be used for the step from propylene to acrolein (and if appropriate acrylic acid) are also compositions of the general formula V

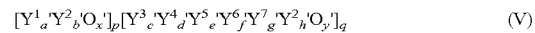
(V)

in which the variables are each defined as follows:
  $Y^1$=only bismuth or bismuth and at least one of the elements tellurium, antimony, tin and copper,
  $Y^2$=molybdenum or tungsten, or molybdenum and tungsten,
  $Y^3$=an alkali metal, thallium and/or samarium,
  $Y^4$=an alkaline earth metal, nickel, cobalt, copper, manganese, zinc, tin, cadmium and/or mercury,
  $Y^5$=iron or iron and at least one of the elements chromium and cerium,
  $Y^6$=phosphorus, arsenic, boron and/or antimony,
  $Y^7$=a rare earth metal, titanium, zirconium, niobium, tantalum, rhenium, ruthenium, rhodium, silver, gold, aluminum, gallium, indium, silicon, germanium, lead, thorium and/or uranium,
  a'=from 0.01 to 8,
  b'=from 0.1 to 30,
  c'=from 0 to 4,
  d'=from 0 to 20,
  e'=from >0 to 20,
  f'=from 0 to 6,
  g'=from 0 to 15,
  h'=from 8 to 16,
  x',y'=numbers which are determined by the valency and frequency of the elements in V other than oxygen and
  p,q=numbers whose p/q ratio is from 0.1 to 10, comprising three-dimensional regions of the chemical composition $Y^1_{a'}Y^2_{b'}O_{x'}$ which are delimited from their local environment owing to their different composition from their local environment, and whose maximum diameter (longest direct line passing through the center of the region and connecting two points on the surface (interface) of the region) is from 1 nm to 100 nm, frequently from 10 nm to 500 nm or from 1 μm to 50 or 25 μm.

Particularly advantageous inventive multimetal oxide compositions V are those in which $Y^1$ is only bismuth.

Among these, preference is given in turn to those of the general formula VI $$[Bi_{a''}Z^2_{b''}O_{x''}]_{p''}[Z^2_{12}Z^3_{c''}Z^4_{d''}Fe_{e''}Z^5_{f''}Z^6_{g''}Z^7_{h''}O_{y''}]_{q''} \quad (VI)$$

in which the variables are each defined as follows:
$Z^2$=molybdenum or tungsten, or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a''=from 0.1 to 1,
b''=from 0.2 to 2,
c''=from 3 to 10,
d''=from 0.02 to 2,
e''=from 0.01 to 5, preferably from 0.1 to 3,
f''=from 0 to 5,
g''=from 0 to 10,
h'' from 0 to 1,
x'',y''=numbers which are determined by the valency and frequency of the elements in VI other than oxygen,
p'',q''=numbers whose p''/q'' ratio is from 0.1 to 5, preferably from 0.5 to 2, and very particular preference is given to those compositions VI in which $Z^2_{b''}$=(tungsten)$_{b''}$ and $Z^2_{12}$=(molybdenum)$_{12}$.

It is also advantageous when at least 25 mol % (preferably at least 50 mol % and more preferably at least 100 mol %) of the total proportion of $[Y^1_aY^2_bO_x]_p$ ($[Bi_{a''}Z^2_{b''}O_{x''}]_{p''}$) of the multimetal oxide compositions V (multimetal oxide compositions VI) suitable in accordance with the invention in the multimetal oxide compositions V (multimetal oxide compositions VI) suitable in accordance with the invention is in the form of three-dimensional regions of the chemical composition $Y^1_aY^2_bO_x[Bi_{a''}Z^2_{b''}O_{x''}]$ which are delimited from their local environment owing to their different chemical composition from their local environment, and whose maximum diameter is in the range from 1 nm to 100 µm.

With regard to the shaping, the statements made for the multimetal oxide composition IV catalysts apply to multimetal oxide composition V catalysts.

The preparation of multimetal oxide active compositions V is described, for example, in EP-A 575 897 and also in DE-A 198 55 913.

The inert support materials recommended above are also useful, inter alia, as inert materials for the dilution and/or delimitation of the appropriate fixed catalyst beds, or as a preliminary bed which protects them and/or heats the gas mixture.

For the second step (the second reaction stage), the heterogeneously catalyzed gas phase partial oxidation of acrolein to acrylic acid, useful active compositions for the catalysts required are, as already stated, in principle all multimetal oxide compositions comprising Mo and V, for example those of DE-A 100 46 928.

A multitude thereof, for example those of DE-A 198 15 281, can be encompassed by the general formula VII.

$$Mo_{12}V_aX^1_bX^2_cX^3_dX^4_eX^5_fX^6_gO_n \quad (VII)$$

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in VII other than oxygen.

Embodiments which are preferred in accordance with the invention among the active multimetal oxides VII are those which are encompassed by the following definitions of the variables of the general formula VII:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements in VII other than oxygen.

However, multimetal oxides VII which are very particularly preferred in accordance with the invention are those of the general formula VIII $$Mo_{12}V_{a'}Y^1_{b'}Y^2_{c'}Y^5_{f'}Y^6_{g'}O_{n'} \quad (VIII)$$

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5,
g'=from 0 to 8 and
n'=a number which is determined by the valency and frequency of the elements in VII other than oxygen.

The multimetal oxide active compositions (VII) which are suitable in accordance with the invention are obtainable in a manner known per se, for example disclosed in DE-A 43 35 973 or in EP-A 714 700.

In principle, multimetal oxide active compositions suitable for the "acrolein→acrylic acid" step, especially those of the general formula VII, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions VII include those compounds which are already oxides and/or those compounds which can be converted to oxides by heating, at least in the presence of oxygen.

The starting compounds for the preparation of multimetal oxide compositions VII can be intimately mixed in dry or in wet form. When they are mixed in dry form, the starting compounds are appropriately used in the form of finely divided powder and subjected to calcining after mixing and, if appropriate, compaction. However, preference is given to intimate mixing in wet form.

This is typically done by mixing the starting compounds with one another in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, especially those of the general formula VII, may be used for the acrolein oxidation either in powder form (for example in a fluidized bed reactor) or shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinders, a wall thickness of from 1 to 3 mm is appropriate. The unsupported catalyst may of course also have spherical geometry, in which case the spherical diameter may be from 2 to 10 mm (e.g. 8.2 mm or 5.1 mm).

The pulverulent active composition or its pulverulent precursor composition which is yet to be calcined can of course also be shaped by applying to preshaped inert catalyst supports. The coating of the support bodies to prepare the coated catalysts is generally performed in a suitable rotatable vessel, as disclosed, for example, by DE-A 2 909 671, EP-A 293 859 or by EP-A 714 700.

To coat the support bodies, the powder composition to be applied is appropriately moistened and is dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders with grit layer. Suitable support bodies include substantially nonporous, surface-roughened, spherical supports made of steatite, whose diameter is from 1 to 10 mm or to 8 mm, preferably from 4 to 5 mm. In other words, suitable spherical geometries may have diameters of 8.2 mm or 5.1 mm. However, suitable support bodies also include cylinders whose length is from 2 to 10 mm and whose external diameter is from 4 to 10 mm. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Suitable support bodies are also in particular rings of geometry 7 mm×3 mm×4 mm (external diameter×length×internal diameter). The fineness of the catalytically active oxide compositions to be applied to the surface of the support body is of course adapted to the desired coating thickness (cf. EP-A 714 700).

Favorable multimetal oxide active compositions to be used for the "acrolein→acrylic acid" step are also compositions of the general formula IX $$[D]_p[E]_q \qquad (IX)$$

in which the variables are each defined as follows:
$E = Z^7{}_{12}Cu_{h''}H_{i''}O_{y'''}$,
$Z^1 = W, Nb, Ta, Cr$ and/or Ce,
$Z^2 = Cu, Ni, Co, Fe, Mn$ and/or Zn,
$Z^3 = Sb$ and/or $B^1$,
$Z^4 = Li, Na, K, Rb, Cs$ and/or H,
$Z^5 = Mg, Ca, Sr$ and/or Ba,
$Z^6 = Si, Al, Ti$ and/or Zr,
$Z^7 = Mo, W, V, Nb$ and/or Ta, preferably Mo and/or W,
a''=from 1 to 8,
b''=from 0.2 to 5,
c''=from 0 to 23,
d''=from 0 to 50,
e''=from 0 to 2,
f''=from 0 to 5,
g''=from 0 to 50,
h''=from 4 to 30,
i''=from 0 to 20 and
x'',y''=numbers which are determined by the valency and frequency of the elements in IX other than oxygen and
p,q=numbers other than zero whose p/q ratio is from 160:1 to 1:1, and which are obtainable by separately preforming a multimetal oxide composition E $$Z^7{}_{12}Cu_{h''}H_{i''}O_{y''} \qquad (E)$$

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the abovementioned elements in the stoichiometry D $$Mo_{12}V_{a''}Z^1{}_{b''}Z^2{}_{c''}Z^3{}_{d''}Z^4{}_{e''}Z^5{}_{f''}Z^6{}_{g''} \qquad (D)$$

(starting composition 2) in the desired p:q ratio, drying the aqueous mixture which may result, and calcining the resulting dry precursor composition before or after drying at temperatures of from 250 to 600° C. to give the desired catalyst geometry.

Preference is given to the multimetal oxide compositions IX in which the preformed solid starting composition 1 is incorporated into an aqueous starting composition 2 at a temperature of <70° C. A detailed description of the preparation of multimetal oxide composition VI catalysts is contained, for example, in EP-A 668 104, DE-A 197 36 105, DE-A 100 46 928, DE-A 197 40 493 and DE-A 195 28 646.

With regard to the shaping, the statements made for the multimetal oxide composition VII catalysts apply to multimetal oxide composition IX catalysts.

Multimetal oxide catalysts which are outstandingly suitable for the "acrolein→acrylic acid" step are also those of DE-A 198 15 281, especially having multimetal oxide active compositions of the general formula I of this document.

Advantageously, unsupported catalyst rings are used for the step from propylene to acrolein and coated catalyst rings for the step from acrolein to acrylic acid.

The performance of the partial oxidation of the process according to the invention, from propylene to acrolein (and acrylic acid if appropriate), may be carried out with the catalysts described, for example, in a single-zone multiple catalyst tube fixed bed reactor, as described by DE-A 44 31 957. In this case, reaction gas mixture and heat carrier (heat exchange medium) may be conducted in cocurrent or in countercurrent viewed over the reactor.

The reaction pressure is typically in the range from 1 to 3 bar and the overall space velocity on the fixed catalyst bed of reaction gas B is preferably from 1500 to 4000 or 6000 l (STP)/l·h or more. The propylene loading (the propylene hourly space velocity on the fixed catalyst bed) is typically from 90 to 200 l (STP)/l·h or to 300 l (STP)/l·h or more. Propylene loadings above 135 l (STP)/l·h or ≧140 l (STP)/l·h, or ≧150 l (STP)/l·h, or ≧160 l (STP)/l·h are particularly preferred in accordance with the invention, since the inventive starting reaction gas mixture for reaction zone B, owing to the presence of unconverted propane and molecular hydrogen, causes favorable hot-spot behavior (all of the aforementioned applies irrespective of the specific selection of the fixed bed reactor).

The flow to the single-zone multiple catalyst tube fixed bed reactor of the charge gas mixture is preferably from above. The heat exchange medium used is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$).

Viewed over the reactor, salt melt and reaction gas mixture may, as already stated, be conducted either in cocurrent or in countercurrent. The salt melt itself is preferably conducted in a meandering manner around the catalyst tubes.

When the flow to the catalyst tubes is from top to bottom, it is appropriate to charge the catalyst tubes with catalyst from bottom to top as follows (for the flow from bottom to top, the charge sequence is appropriately reversed):

first, to a length of from 40 to 80 or to 60% of the catalyst tube length, either only catalyst or a mixture of catalyst and inert material, the latter, based on the mixture, making up a proportion by weight of up to 30 or up to 20% by weight (section C);

following this, to a length of from 20 to 50 or to 40% of the total tube length, either only catalyst or a mixture of catalyst and inert material, the latter, based on the mixture, making up a proportion by weight of up to 40% by weight (section B); and finally, to a length of from 10 to 20% of the total tube length, a bed of inert material (section A) which is preferably selected such that it causes a very small pressure drop.

Section C is Preferably Undiluted.

The aforementioned charge variant is especially appropriate when the catalysts used are those according to Research Disclosure No. 497012 of Aug. 29, 2005, Example 1 of DE-A 100 46 957 or according to Example 3 of DE-A 100 46 957 and the inert material used is steatite rings having the geometry 7 mm×7 mm×4 mm (external diameter×height×internal diameter). With regard to the salt bath temperature, the statements of DE-A 4 431 957 apply.

However, the performance of the partial oxidation in reaction zone B, from propylene to acrolein (and acrylic acid if appropriate), may also be carried out with the catalysts described, for example, in a two-zone multiple catalyst tube fixed bed reactor, as described by DE-A 199 10 506, DE-A 10 2005 009 885, DE-A 10 2004 032 129, DE-A 10 2005 013 039 and DE-A 10 2005 009 891, and also DE-A 10 2005 010 111. In both of the above-described cases (and quite generally in the process according to the invention), the propene conversion achieved in single pass is normally at values of ≧90 mol %, or ≧95 mol %, and the selectivity of acrolein formation at values of ≧90 mol %. Advantageously in accordance with the invention, the inventive partial oxidation of propene to acrolein, or acrylic acid or mixtures thereof, is effected as described in EP-A 1 159 244 and most preferably as described in WO 04/085363 and in WO 04/085362.

The documents EP-A 1 159 244, WO 04/085363 and WO 04/085362 are considered to be an integral part of this document.

In other words, a partial oxidation of propylene to acrolein (and acrylic acid if appropriate) to be carried out in reaction zone B can be carried out particularly advantageously over a fixed catalyst bed having increased propylene loading and at least two temperature zones.

In this regard, reference is made, for example, to EP-A 1 159 244 and WO 04/085362.

The performance of the second step in the case of a two-stage partial oxidation of propylene to acrolein, i.e. the partial oxidation of acrolein to acrylic acid, may be carried out with the catalysts described, for example, in a one-zone multiple catalyst tube fixed bed reactor as described in DE-A 44 31 949. In this reaction stage, reaction gas mixture and heat carrier can be conducted in cocurrent viewed over the reactor. In general, the product gas mixture of the preceding inventive propylene partial oxidation to acrolein is in principle conducted as such (if appropriate after intermediate cooling (this may be effected indirectly or directly by, for example, secondary oxygen addition (or secondary air addition in a manner less preferred in accordance with the invention)) thereof), i.e. without secondary component removal, into the second reaction stage, i.e. into the acrolein partial oxidation.

The molecular oxygen required for the second step, the acrolein partial oxidation, may already be present in the reaction gas B starting mixture for the propylene partial oxidation to acrolein. However, it may also be added partly or fully directly to the product gas mixture of the first reaction stage, i.e. the propylene partial oxidation to acrolein (this can be effected in the form of secondary air, but may preferably be effected in the form of pure oxygen or of mixtures of inert gas and oxygen (with preferably ≦50% by volume, or ≦40% by volume, or ≦30% by volume, or ≦20% by volume, or ≦10% by volume, or ≦5% by volume, or ≦2% by volume)). Irrespective of the procedure, the charge gas mixture (starting reaction gas mixture) of such a partial oxidation of acrolein to acrylic acid advantageously has the following contents:

| | |
|---|---|
| from 3 to 25% by volume of | acrolein, |
| from 5 to 65% by volume of | molecular oxygen, |
| from 6 to 70% by volume of | propane, |

-continued

| | |
|---|---|
| from 0.3 to 20% by volume of | molecular hydrogen and |
| from 8 to 65% by volume of | steam. |

The aforementioned starting reaction gas mixture preferably has the following contents:

| | |
|---|---|
| from 5 to 14% by volume of | acrolein, |
| from 6 to 25% by volume of | molecular oxygen, |
| from 6 to 60% by volume of | propane, |
| from 2 to 18% by volume of | molecular hydrogen and |
| from 7 to 35% by volume of | steam. |

The aforementioned starting reaction gas mixture most preferably has the following contents:

| | |
|---|---|
| from 6 to 12% by volume of | acrolein, |
| from 8 to 20% by volume of | molecular oxygen, |
| from 20 to 55% by volume of | propane, |
| from 6 to 15% by volume of | molecular hydrogen and |
| from 11 to 26% by volume of | steam, | the preferred ranges applying independently of one another, but advantageously being realized simultaneously. The nitrogen content in the aforementioned mixtures will generally be $\leq 20\%$ by volume, preferably $\leq 15\%$ by volume, more preferably $\leq 10\%$ by volume and most preferably $\leq 5\%$ by volume. The ratio of the molar amounts of $O_2$ and acrolein present in the charge gas mixture for the second oxidation stage, $O_2$: acrolein, is, advantageously in accordance with the invention, generally $\geq 0.5$ and $\leq 2$, frequently $\geq 1$ and $\leq 1.5$.

The $CO_2$ content of the charge gas mixture for the second oxidation stage may be from 1 to 40% by volume, or from 2 to 30% by volume, or from 4 to 20% by volume, or frequently from 6 to 18% by volume.

As in the first reaction stage (propylene→acrolein), the reaction pressure in the second reaction stage (acrolein→acrylic acid) too is typically in the range from 1 to 3 bar and the total space velocity on the fixed catalyst bed of (starting) reaction gas mixture is preferably from 1500 to 4000 or 6000 l (STP)/l·h or more. The acrolein loading (the acrolein hourly space velocity on the fixed catalyst bed) is typically from 90 to 190 l (STP)/l·h, or to 290 l (STP)/l·h or more. Acrolein loadings above 135 l (STP)/l·h, or $\geq 140$ l (STP)/l·h, or $\geq 150$ l (STP)/l·h, or $\geq 160$ l (STP)/l·h are particularly preferred, since the starting reaction gas mixture to be used in accordance with the invention, owing to the presence of propane and molecular hydrogen, likewise results in favorable hotspot behavior.

The acrolein conversion based on single pass of starting reaction gas mixture through the fixed catalyst bed of the second oxidation stage is appropriately normally $\geq 90$ mol % and the accompanying selectivity of acrylic acid formation $\geq 90$ mol %.

The flow to the single-zone multiple catalyst tube fixed bed reactor of the charge gas mixture is likewise preferably from above. The heat exchange medium used in the second stage too is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$). Viewed over the reactor, as already stated, salt melt and reaction gas mixture may be conducted either in cocurrent or in countercurrent. The salt melt itself is preferably conducted in a meandering manner around the catalyst tubes.

When the flow to the catalyst tubes is from top to bottom, it is appropriate to charge the catalyst tubes with catalyst from bottom to top as follows:

first, to a length of from 50 to 80 or to 70% of the catalyst tube length, either only catalyst or a mixture of catalyst and inert material, the latter, based on the mixture, making up a proportion by weight of up to 30 (or up to 20) % by weight (section C);

following this, to a length of from 20 to 40% of the total tube length, either only catalyst or a mixture of catalyst and inert material, the latter, based on the mixture, making up a proportion by weight of up to 50 or up to 40% by weight (section B); and finally, to a length of from 5 to 20% of the total tube length, a bed of inert material (section A) which is preferably selected such that it causes a very small pressure drop.

Section C is preferably undiluted. As is quite generally the case for the heterogeneously catalyzed gas phase partial oxidation of acrolein to acrylic acid (especially at high acrolein loadings on the fixed catalyst bed and high steam contents of the charge gas mixture), section B may also consist of two successive catalyst dilutions (for the purpose of minimizing hotspot temperature and hotspot temperature sensitivity). From bottom to top, first with up to 30 (or 20) % by weight of inert material and subsequently with from >20% by weight to 50 or to 40% by weight of inert material. Section C is then preferably undiluted.

For flow to the catalyst tubes from bottom to top, the catalyst tube charge is appropriately reversed.

The aforementioned charge variant is especially appropriate when the catalysts used are those according to preparation example 5 of DE-A 100 46 928 or those according to DE-A 198 15 281 and the inert material used is steatite rings having the geometry 7 mm×7 mm×4 mm or 7 mm×7 mm×3 mm (in each case external diameter×height×internal diameter). With regard to the salt bath temperature, the statements of DE-A 443 19 49 apply. It is generally selected in such a way that the acrolein conversion achieved in single pass is normally $\geq 90$ mol %, or $\geq 95$ mol % or 99 mol %. However, the performance of the partial oxidation of acrolein to acrylic acid may also be carried out with the catalysts described, for example, in a two-zone multiple catalyst tube fixed bed reactor as described in DE-A 199 10 508. For the acrolein conversion, the above statements apply. Also in the case in which an acrolein partial oxidation as described above is carried out as the second stage of a two-stage propylene partial oxidation to acrylic acid in a two-zone multiple catalyst tube fixed bed reactor, the charge gas mixture (starting reaction gas mixture) will appropriately be obtained directly by using the product gas mixture of the partial oxidation directed to the first step (propylene→acrolein) (if appropriate after indirect or direct (for example by supplying secondary oxygen) intermediate cooling thereof) (as has already been described above). The oxygen required for the acrolein partial oxidation is preferably added in the form of pure molecular oxygen (if appropriate also in the form of air or in the form of a mixture of molecular oxygen and an inert gas having an inert gas fraction of preferably $\leq 50\%$ by volume, more preferably $\leq 40\%$ by volume, or $\leq 30\%$ by volume, or $\leq 20\%$ by volume, even better $\leq 10\%$ by volume, or $\leq 5\%$ by volume, or $\leq 2\%$ by volume) and, for example, added directly to the product gas mixture of the first step of the two-stage partial oxidation (propylene→acrolein). However, it may also, as already described, already be present in the starting reaction gas mixture for the first reaction stage.

In a two-stage partial oxidation of propylene to acrylic acid with direct further use of the product gas mixture of the first step of the partial oxidation to charge the second step of the partial oxidation, two one-zone multiple catalyst tube fixed bed reactors (at high reactant loading on the catalyst bed, as is quite generally the case, preference is given to countercurrent mode between reaction gas and salt bath (heat carrier) viewed over the tube bundle reactor) or two two-zone multiple catalyst tube fixed bed reactors will generally be connected in series. A mixed series connection (one-zone/two-zone or vice versa) is also possible.

Between the reactors may be disposed an intermediate cooler which may if appropriate comprise inert beds which can perform a filter function. The salt bath temperature of multiple catalyst tube reactors for the first step of the two-stage partial oxidation of propylene to acrylic acid is generally from 300 to 400° C. The salt bath temperature of multiple catalyst tube reactors for the second step of the partial oxidation of propylene to acrylic acid, the partial oxidation of acrolein to acrylic acid, is usually from 200 to 350° C. In addition, the heat exchange media (preferably salt melts) are normally conducted through the relevant multiple catalyst tube fixed bed reactors in such amounts that the difference between their input temperature and their output temperature is generally $\leq 5°$ C. As already mentioned, both steps of the partial oxidation of propylene to acrylic acid may also be implemented in one reactor over one charge, as described in DE-A 101 21 592.

It should also be mentioned here that a portion of the reaction gas B starting mixture for the first step ("propylene→acrolein") may be residual gas I coming from separation zone I and/or residual gas I aftertreated in accordance with the invention.

However, aforementioned residual gases I are, preferably in accordance with the invention, recycled exclusively as cycle gas I into the heterogeneously catalyzed propane dehydrogenation in reaction zone A, and appropriately exclusively as a constituent of the reaction gas A starting mixture. For the sake of completeness, it is emphasized here that fresh propane may be metered additionally into both the charge gas mixture for the first oxidation stage and the charge gas mixture for the second oxidation stage, or else only one of the two. It is not preferred in accordance with the invention, but it may be favorable in some cases in order to rule out ignitability of the charge gas mixtures.

Overall, a tube bundle reactor within which the catalyst charge changes appropriately along the individual catalyst tubes with completion of the first reaction step (such two-stage propylene partial oxidations in a single reactor are taught, for example, by EP-A 911 313, EP-A 979 813, EP-A 990 636 and DE-A 28 30 765) forms the simplest implementation form of the two oxidation stages for the two steps of the partial oxidation from propylene to acrylic acid. If appropriate, the charge of the catalyst tubes with catalyst is interrupted by an inert material bed.

However, preference is given to implementing the two oxidation stages in the form of two tube bundle systems connected in series. These may be disposed in one reactor, in which case the transition from one tube bundle to the other tube bundle is formed by a bed of inert material which is not accommodated in the catalyst tube (and is appropriately accessible on foot). While the catalyst tubes are generally flowed around by a heat carrier, this does not reach an inert material bed accommodated as described above. Advantageously, the two catalyst tube bundles are therefore accommodated in spatially separate reactors. In general, an intermediate cooler is disposed between the two tube bundle reactors in order to reduce any acrolein postcombustion proceeding in the product gas mixture which leaves the first oxidation zone. The reaction temperature in the first reaction stage (propylene→acrolein) is generally from 300 to 450° C., preferably from 320 to 390° C. The reaction temperature in the first reaction stage (acrolein→acrylic acid) is generally from 200 to 370° C., frequently from 220 to 330° C. The reaction pressure in both oxidation stages is appropriately from 0.5 to 5 bar, advantageously from 1 to 3 bar. The loading (l (STP)/l·h) on the oxidation catalysts of reaction gas in both reaction stages is frequently from 1500 to 2500 l (STP)/l·h or to 4000 l (STP)/l·h. The loading of propylene or acrolein may be from 100 to 200 or 300 and more l (STP)/l·h.

In principle, the two oxidation stages in the process according to the invention may be configured as described, for example, in DE-A 198 37 517, DE-A 199 10 506, DE-A 199 10 508 and DE-A 198 37 519.

In both reaction stages, an excess of molecular oxygen relative to the amount required in accordance with the reaction stoichiometry has an advantageous effect on the kinetics of the particular gas phase partial oxidation and on the catalyst lifetime.

In principle, it is also possible to realize the heterogeneously catalyzed gas phase partial oxidation of propylene to acrylic acid to be carried out in accordance with the invention in a single tube bundle reactor as follows. Both reaction steps proceed in an oxidation reactor which is charged with one or more catalysts whose active composition is a multimetal oxide which comprises the elements Mo, Fe and Bi and is capable of catalyzing the reaction of both reaction steps. This catalyst charge can of course change continuously or abruptly along the reaction coordinate. Of course, it is possible in one embodiment of an inventive two-stage partial oxidation of propylene to acrylic acid in the form of two oxidation stages connected in series to partly or fully remove carbon dioxide and steam which have formed as a by-product in the first oxidation stage and are present in the product gas mixture leaving the first oxidation stage from this product gas mixture, if required, before it is passed on into the second oxidation stage. Preference is given in accordance with the invention to selecting a procedure which does not provide for such a removal.

Useful sources for intermediate oxygen feeding carried out between the two oxidation stages are, as already stated, in addition to air (preferred), either pure molecular oxygen or molecular oxygen diluted with inert gas such as $CO_2$, CO, noble gases, $N_2$ and/or saturated hydrocarbons. Preferably in accordance with the invention, the oxygen source comprises $\leq 50\%$ by volume, preferably $\leq 40\%$ by volume, more preferably $\leq 30\%$ by volume, even more preferably $\leq 20\%$ by volume, better $\leq 10\%$ by volume or $\leq 5\%$ by volume, or $\leq 2\%$ of gases other than molecular oxygen.

In the process according to the invention, metering of, for example, cold oxygen source to the product gas mixture of the first partial oxidation stage can also bring about cooling thereof by a direct route before it is used further as a constituent of a starting reaction gas mixture for the second partial oxidation stage.

Advantageously in accordance with the invention, the partial oxidation of acrolein to acrylic acid is effected as described in EP-A 1 159 246 and most preferably as described in WO 04/085365 and in WO 04/085370. However, preference is given in accordance with the invention to using, as the starting reaction gas mixture comprising acrblein, a starting reaction gas mixture which is the product gas mixture of an inventive first-stage partial oxidation of propylene to acrolein, which has if appropriate been supplemented with sufficient secondary air that the ratio of molecular oxygen to acrolein in the resulting starting reaction gas mixture is in each case from 0.5 to 1.5. The documents EP-A 1 159 246, WO 04/08536 and WO 04/085370 are considered to be an integral part of this document.

In other words, the inventive partial oxidation of acrolein to acrylic acid can be carried out with increased acrolein loading advantageously over a fixed catalyst bed which has at least two temperature zones.

Overall, a two-stage partial oxidation of propylene to acrylic acid will preferably be carried out as described in EP-A 1 159 248 or in WO 04/085367 or WO 04/085369.

The product gas B which leaves the partial oxidation to be carried out in accordance with the invention (after the first and/or the second reaction stage) comprises substantially acrolein or acrylic acid or a mixture thereof as the target product, unconverted propane, molecular hydrogen, steam (formed as a by-product and/or used additionally as a diluent gas), any unconverted molecular oxygen (with a view to the lifetime of the catalysts used, it is typically favorable when the oxygen content in the product gas mixture of both partial oxidation stages is, for example, still from at least 1.5 to 4% by volume), and also other by-products or secondary components having higher and lower boiling points than water (for example CO, $CO_2$, lower aldehydes, lower alkanecarboxylic acids (e.g. acetic acid, formic acid and propionic acid), maleic anhydride, benzaldehyde, aromatic carboxylic acids and aromatic carboxylic anhydrides (e.g. phthalic anhydride and benzoic acid), in some cases further hydrocarbons, for example $C_4$ hydrocarbons (e.g. butene-1 and possibly other butenes), and in some cases further inert diluent gases, for example $N_2$).

Useful processes for removing target product, water and secondary components having higher boiling points than water for the process according to the invention in the first separation zone I are in principle all processes known in this regard in the prior art. An essential feature of these processes is that the target product is converted from the gaseous to the condensed phase, for example by absorptive and/or condensative measures, and the condensates or absorbates are subsequently worked up by extractive, distillative, crystallative, and/or desorptive measures for the purpose of further target product removal. Together with the target products and/or following the conversion of the target product to the condensed phase, these processes typically also convert steam and secondary components having higher boiling points than water present in reaction gas B to the condensed phase and hence remove them (preferably in accordance with the invention, an amount of steam is converted to the condensed phase which is at least 70 mol %, preferably at least 80 mol %, better at least 90 mol % and more preferably at least 95 mol % of the total amount of steam formed in reaction zone B (or more preferably of the entire amount-present in product gas B)).

Useful absorbents include, for example, water, aqueous solutions and/or organic solvents (for example mixtures of diphenyl and diphenyl ether or of diphenyl, diphenyl ether and o-dimethyl phthalate). This "condensation" (removal) of target product, water and secondary components having higher boiling points than water normally leaves a residual gas which is not converted to the condensed phase and comprises constituents of product gas B which have a lower boiling point than water and are comparatively difficult to condense. These are typically those components in particular whose boiling point at standard pressure (1 bar) is $\leq -30°$ C. (their total content in the residual gas is generally $\geq 60\%$ by volume, frequently $\geq 70\%$ by volume, in many cases $\geq 80\%$ by volume, but usually $\leq 90\%$ by volume). These include primarily unconverted propane, molecular hydrogen, carbon dioxide, any unconverted propylene, any unconverted molecular oxygen and other secondary components having lower boiling points than water, for example CO, ethane, methane, in some cases $N_2$, in some cases noble gases (e.g. He, Ne, Ar etc.). To a slight extent, the residual gas may also comprise acrylic acid, arolein and/or $H_2O$. Preferably in accordance with the invention, the residual gas comprises $\leq 10\%$ by volume, advantageously $\leq 5\%$ by volume and particularly advantageously $\leq 3\%$ by volume of steam. This aforementioned residual gas normally forms (based on the amount of propane present therein) the majority (typically at least 80% or at least 90% or at least 95% or more) of the residual gas formed in the first separation zone I and is referred to in this document as (main) residual gas I.

Especially when the target product is condensed by absorbing by means of one organic solvent, at least a second residual gas comprising unconverted propane and any unconverted propylene is generally obtained in separation zone I (based on propane present therein, its amount in comparison to the amount of (main) residual gas I is normally substantially lower (generally $\leq 20\%$, usually $\leq 10\%$, or $\leq 5\%$, or $\leq 1$)). This is attributable to the condensed phase which forms also absorbing a certain amount of unconverted propane and any unconverted propylene.

In the further course of the extractive, distillative, crystallative and/or desorptive removal of the target product from the condensed phase, this unconverted propane and any propylene is normally recycled as a constituent of at least one further gas phase and is referred to in this document as (secondary) residual gas I.

In this case, the sum of (main) residual gas I and (secondary) residual gas I forms the total amount of residual gas I. When no (secondary) residual gas I is obtained in separation zone I the (main) residual gas I is automatically the total amount of residual gas I (also known as (total) residual gas I).

Preferably in accordance with the invention, the target product is converted from product gas B to the condensed phase by fractional condensation. This is especially true when the target product is acrylic acid. However, suitable processes for target product removal are in principle, for example, all of the absorptive and/or condensative processes for "target product condensation" and further workup of the "condensate" described in the documents DE-A 102 13 998, DE-A 22 63 496, U.S. Pat. No. 3,433,840 (processes described in the aforementioned documents are especially recommended for acrolein removal), EP-A 1 388 533, EP-A 1 388 532, DE-A 102 35 847, EP-A 792 867, WO 98/01415, EP-A 1 015 411, EP-A 1 015 410, WO 99/50219, WO 00/53560, WO 02/09839, DE-A 102 35 847, WO 03/041833, DE-A 102 23 058, DE-A 102 43 625, DE-A 103 36 386, EP-A 854 129, U.S. Pat. No. 4,317,926, DE-A 198 37 520, DE-A 196 06 877, DE-A 190 50 1325, DE-A 102 47 240, DE-A 197 40 253, EP-A 695 736, EP-A 982 287, EP-A 1 041 062, EP-A 117 146, DE-A 43 08 087, DE-A 43 35 172, DE-A 44 36 243, DE-A 199 24 532, DE-A 103 32 758 and DE-A 199 24 533. An acrylic acid removal can also undertaken as in EP-A 982 287, EP-A 982 289, DE-A 103 36 386, DE-A 101 15 277, DE-A 196 06 877, DE-A 197 40 252, DE-A 196 27 847, EP-A 920 408, EP-A 1 068 174, EP-A 1 066 239, EP-A 1 066 240, WO 00/53560, WO 00/53561, DE-A 100 53 086 and EP-A 982 288. Preference is given to removing as in FIG. 7 of WO/0196271 or as described in DE-A 10 2004 032 129 and their equivalent patents. Suitable removal methods are also the processes described in the documents WO 04/063138, WO 04/35514, DE-A 102 43 625 and DE-A 102 35 847. The further processing of crude acrylic acid obtained can be effected, for example, as described in the documents WO 01/77056, WO 03/041832, WO 02/055469, WO 03/078378 and WO 03/041833.

A common feature of the above separating processes is (as already mentioned) a stream of residual gas I which comprises mainly those constituents of product gas B whose boiling point at standard pressure (1 bar) is lower than that of water and is usually $\leq -30°$ C. (i.e. the constituents which are difficult to condense or else volatile) normally remains, for example, at the top of the particular separating column comprising separating internals, into whose lower section product gas B is fed, for example, normally after preceding direct and/or indirect cooling thereof. However, residual gas I may, for example, also still comprise constituents such as steam and acrylic acid.

In the lower section of the separating column, normally mainly the less volatile constituents of product gas B are obtained, including the particular target product, in condensed phase. Condensed aqueous phase is generally removed via side draw and/or via the bottom.

Typically, (main) residual gas I comprises the following contents:

| | |
|---|---|
| from 1 to 20% by volume of | $H_2O$, |
| from 40 to 90% by volume of | Propane, |
| from 0 to 10% by volume of | $O_2$, |
| from 5 to 30% by volume of | $CO_2$ and |
| from >0 to 2% by volume of | CO. |

The content of acrolein and acrylic acid is generally in each case <1% by volume.

It is then required in accordance with the invention that the residual gas I obtained in separation zone I is subjected to certain aftertreatment measures. It is an essential feature of the invention that the particular aftertreatment measure need not necessarily be carried out on the entirety of residual gas I. In other words, it may be appropriate in accordance with the invention to carry out the aftertreatment measure only on a portion (for example only the (main) residual gas I) of the total amount of residual gas I. In this case, the sum of the untreated portion of the total amount of residual gas I and of the residual gas which comprises propane and remains after the aftertreatment measure has been carried out on the other portion of the total amount of the residual gas I forms the total amount of aftertreated residual gas I (the "new" residual gas I) which can be subjected to further inventive aftertreatment in a corresponding manner (the portions mentioned may also have different chemical composition). From the total amount of (aftertreated) residual gas I which comprises unconverted propane and remains after all aftertreatment measures considered to be necessary in the present case have been carried out, at least a portion is recycled in accordance with the invention into reaction zone A as at least one of the at least two feed streams comprising propane. Another portion (if appropriate also a non-aftertreated portion of residual gas I) may, if appropriate, be recycled into the first and/or second oxidation stage of reaction zone B in order to adjust the explosion behavior of the reaction gas advantageously as a constituent of the particular charge gas.

However, advantageously in accordance with the invention, the amount of residual gas I which has been aftertreated in accordance with the invention and is recycled in accordance with the invention into reaction zone A as at least one of the at least two feed streams comprising propane will be measured such that it comprises at least 80 mol %, preferably at least 85 mol %, better at least 90 mol %, or at least 92 mol %, or at least 94 mol %, or at least 96 mol %, or at least 98 mol % of the propane conducted out of reaction zone B with product gas B. This recycling need not necessarily be effected to one and the same point in reaction zone A. Instead, it can also be done via a plurality of different feed points distributed over reaction zone A.

In the context of the above statements, an essential feature of the invention is that the sequence of aftertreatment measures carried out on residual gas I is arbitrary in accordance with the invention. In other words, instead of first discharging a portion of residual gas I and then subjecting the remaining amount to $CO_2$ scrubbing, it would also be possible, for example, to effect the $CO_2$ scrubbing first and to discharge a portion from the residual gas I scrubbed in this way.

However, in a manner advantageous in accordance with the invention, the sequence of aftertreatment measures which follows will be observed (they relate in particular to the aftertreatment of the (main) residual gas I).

First, a portion of residual gas I will be discharged (the discharge is necessary especially in order to discharge inert components introduced additionally with the feed of molecular oxygen to the overall process). This discharged amount (the amount of residual gas I discharged is generally sent to an off gas combustion) may have the same composition as the residual gas I itself. This will generally be the case when the amount of propane present in the discharged residual gas I per unit time, based on the amount of fresh propane fed into the process per unit time, is $\leq 30$ mol %, better $\leq 25$ mol % or $\leq 20$ mol %, or $\leq 15$ mol %, preferably $\leq 10$ mol %, more preferably $\leq 5$ mol % and most preferably $\leq 3$ mol % or $\leq 1$ mol %.

Were the amount of propane discharged to be higher than the aforementioned values, or even in the case of the aforementioned values, the discharge can also be carried out such that the amount of propane and any propylene present in the amount of residual gas I to be discharged is removed prior to the discharge of the discharge amount, as a result of which propane and any propylene removed in this way remains part of residual gas I aftertreated in accordance with the invention.

A simple means for the aforementioned removal consists, for example, in contacting the appropriate amount of residual gas I with a (preferably high-boiling) organic solvent (preferably a hydrophobic solvent, for example tetradecane or mixtures of $C_8$-$C_{20}$-alkanes), in which propane and propylene (appropriately preferentially compared to the other constituents of residual gas I) are absorbed (for example by simply passing it through). The propane and (any) propylene are recovered by subsequent desorption (under reduced pressure) distillation and/or stripping with a gas which is not disruptive in reaction zone A (for example steam, molecular oxygen, molecular hydrogen and/or other inert gas (for example also air)), and they are added to the aftertreated residual gas I. Specifically, the procedure may be as in the analogous absorptive removal of propane from product gas A described in DE-A 10 2004 032 129. When the above-described removal, which is less preferred in accordance with the invention, is undertaken in the process according to the invention, it will always extend only to a portion of residual gas I and thus only to a portion of the propane present in product gas B. Preferably in accordance with the invention, the aforementioned propane portion is $\leq 50$ mol %, more preferably $\leq 40$ mol %, more preferably $\leq 30$ mol %, more preferably $\leq 20$ mol %, even more preferably $\leq 10$ mol % and most preferably $\leq 5$ mol %.

After a portion of residual gas I has been discharged, $CO_2$ present therein will be scrubbed out of at least a portion of residual gas I (in a second separation zone II). When residual gas I also comprises CO and $O_2$, it is possible (with simultaneous chemical reduction of the molecular oxygen) to oxidize CO present beforehand in residual gas I selectively to $CO_2$, for example by passing it over appropriate catalysts (if required, it is also possible to meter molecular oxygen required for this purpose beforehand to residual gas I). The catalysts recommended in WO 01/60738 (complex oxides of stoichiometry $Cu_xCe_{1-x}O_{2-y}$, where x=from 0.01 to 0.3 and y≧x), this is also possible in the presence of molecular hydrogen. However, such a CO conversion is not preferred in accordance with the invention. This is because CO remaining in cycle gas I would in any case at least partly be oxidized to $CO_2$ in the downstream circulation loop in reaction zones A and/or B, and thus has a natural outlet in the aforementioned $CO_2$ scrubbing. However, the CO conversion can also be accompanied simultaneously by a reduction of $O_2$ present in residual gas I with $H_2$ present in residual gas I. This reduction can also be implemented in a singular manner.

In general, it is sufficient in accordance with the invention only to scrub a portion of the $CO_2$ present in residual gas I out of it. Advantageously, the $CO_2$ scrubbing will be undertaken at elevated pressure (typically from 3 to 50 bar, better from 5 to 30 bar, preferably from 8 to 20 bar, more preferably from 10 to 20 or to 15 bar), and, appropriately in accordance with the invention, by means of a basic (in the Brønsted sense) liquid.

Useful such basic liquids include, for example, organic amines such as monoethanolamine, aqueous solutions of organic amines, for example of monoethanolamine, aqueous alkali metal hydroxide solutions or aqueous alkali metal carbonate solutions or aqueous solutions of alkali metal carbonates and alkali metal hydrogencarbonates (cf., for example, also WO 05/05347). Preferably in accordance with the invention, an aqueous solution comprising $K_2CO_3$ will be used for $CO_2$ scrubbing. Useful such aqueous solutions include, for example, solutions of $K_2CO_3$ in water, or of $K_2CO_3$ and $KHCO_3$ in water, or of $K_2CO_3$, $KHCO_3$ and KOH in water. Advantageously, such an aqueous potassium carbonate solution has the solids content of from 10 to 30 or 40% by weight, more preferably of from 20 to 25% by weight. Addition of small amounts of alkali metal hydroxide (e.g. KOH) allows the aqueous alkali metal carbonate solution additionally to be made alkaline prior to the scrubbing in order to neutralize any carboxylic acids (e.g. acetic acid, formic acid, acrylic acid) present in small amounts in residual gas I. Favorable aqueous scrubbing solutions are also those which comprise $KHCO_3$ and $K_2CO_3$ dissolved in a weight ratio of approx. 1:2, their solids content advantageously being from 20 to 25% by weight. With absorption of $CO_2$ and water, one molar unit of $K_2CO_3$ is converted to two molar units of $KHCO_3$ in the course of the scrubbing ($K_2CO_3 + H_2O + CO_2 \rightarrow 2\ KHCO_3$).

Instead of carrying out the $CO_2$ scrubbing by means of a basic liquid, it is also possible to carry out the $CO_2$ scrubbing, for example, with $CO_2$-clathrate formation according to the teaching of EP-A 900 121.

Appropriately in accordance with the invention, the $CO_2$ scrubbing will be undertaken in a wash column and in countercurrent. The residual gas I to be scrubbed generally flows from the bottom upward and the scrubbing liquid from the top downward in the scrubbing column. In a manner known per se, the scrubbing column comprises internals which increase the heat exchange surface area. These may be random packaging, mass transfer trays (for example sieve trays) and/or structure packaging:

At the top of the scrubbing column, the scrubbed residual gas I is advantageously discharged and the aqueous solution comprising predominantly potassium hydrogencarbonate (or an aqueous $CO_2$-Clathrat solution) is, for example, advantageously withdrawn from the bottom of the scrubbing column. For example, the bottoms solution may comprise $KHCO_3$ and $K_2CO_3$ dissolved in a weight ratio of 2.5:1.

Introduction of hot steam into the aqueous potassium hydrogencarbonate solution allows the hydrogencarbonate to be dissociated thermally (to carbonate and $CO_2$, $H_2O$) and the $CO_2$ released to be driven out. The aqueous potassium carbonate solution recovered in this way can, generally after evaporation of steam condensed in the course of dissociation, be recycled into the $CO_2$ scrubbing to be carried out as described. The evaporation of the condensed steam can also be operated continuously by evaporators integrated into the column. The aforementioned dissociation is appropriately likewise performed in a column comprising internals which increase the heat exchange surface area (for example (sieve) tray, column with structured packing and/or column with random packing). Also advantageous here is countercurrent operation. The hot steam is advantageously fed in the lower section of the column and the aqueous potassium carbonate solution is advantageously introduced at the top of the column.

While the $CO_2$ scrubbing is preferably carried out at low temperatures, the hydrogen-carbonate dissociation is preferably carried out at elevated temperatures. In the described integrated system of $CO_2$ scrubbing, dissociation of the scrubbing solution and reuse as a scrubbing liquid, the dissociation is appropriately effected by means of steam which has a temperature of from 130 to 160° C., preferably of from 140 to 150° C. The aqueous solution to be dissociated is appropriately introduced with a temperature of from 80 to 120° C., more preferably from 90 to 110° C. Conversely, residual gas I is, advantageously in accordance with the invention, conducted into the scrubbing column at a temperature of from 60 to 90° C., more preferably from 70 to 80° C., and the scrubbing liquid introduced at a temperature of from 70 to 90° C., preferably from 75 to 85° C.

Especially when only a portion of residual gas I is subjected to $CO_2$ scrubbing, it is advantageous to carry out the compression of residual gas I to the pressure preferred for the $CO_2$ scrubbing in a plurality of stages (for example with the aid of a multistage radial compressor; beyond each compression stage, compressed gas can be withdrawn). Typically, residual gas I leaves separation zone I in the process according to the invention with a pressure of $\geq 1$ bar and $\leq 2.5$ bar, preferably $\leq 2.0$ bar. The heterogeneously catalyzed dehydrogenation in reaction zone A is effected advantageously at a pressure of from $\geq 2$ to $\leq 4$ bar, preferably from $\geq 2.5$ to $\leq 3.5$ bar. Favorably in accordance with the invention, reaction zone B is operated at a pressure of $\geq 1$ bar and $\leq 3$ bar, preferably $\geq 1.5$ and $\leq 2.5$ bar. The preferred working pressures for $CO_2$ scrubbing are from 3 to 50 bar, or 5 to 30 bar, or from 8 to 20 bar, preferably from 10 to 20 or to 15 bar.

Appropriately in accordance with the invention, a compression of the residual gas to the working pressure in reaction zone A (for example from 1.2 to 3.2 bar) is then carried out in a first compression stage with the aid of a multistage, for example, turbo-compressor (radial compressor, for example of the MH4B type from Mannesmann DEMAG, Germany) (also referred to here as cycle gas I compressor). When it is not the entirety of residual gas I that is subjected to $CO_2$ scrubbing, the residual gas I compressed as described is appropriately divided into two portions of identical composition. The proportions may amount, for example, to from 70 to 30% of the total amount. The portion which is not to be subjected to $CO_2$ scrubbing is then immediately ready for recycling into reaction zone A. Only the other portion is compressed further to the working pressure contemplated for the $CO_2$ scrubbing. This can be done in only one further compression stage. However, advantageously in accordance with the invention, at least two further compression stages will be employed for this purpose. This is because a simultaneous temperature increase of the gas is associated with its compression. Conversely, the decompression (expansion) of the $CO_2$-scrubbed residual gas I to the working pressure appropriate for recycling into reaction zone A is associated with cooling of the $CO_2$-scrubbed residual gas I. When the decompression is likewise carried out in a plurality of stages, it is possible before the next stage in each case to undertake indirect heat exchange between heated, compressed unscrubbed residual gas I and cooled, expanded, $CO_2$-scrubbed residual gas I. Such a heat exchange may also be employed actually before the first expansion. As a consequence of the indirect heat exchange, condensation of steam still present if appropriate in residual gas I can occur therein. The aforementioned expansions are, advantageously from an application point of view, carried out in (advantageously likewise multistage) expansion turbines (this serves to recover compression energy). For each compression or expansion stage, the difference between inlet and outlet pressure may, for example, be from 2 to 10 bar.

In general, at least 50 mol %, usually at least 60 mol %, or at least 80 mol-% and in many cases at least or more than 90% by volume of the $CO_2$ present in residual gas I are scrubbed out in separation zone II.

Appropriately, the amount of $CO_2$ scrubbed out corresponds to the total amount of $CO_2$ formed in reaction zones A and B.

In general, $CO_2$-scrubbed residual gas still comprises from 1 to 20% by volume, in many cases from 5 to 10% by volume of $CO_2$.

Before the $CO_2$-scrubbed residual gas I is decompressed, it can also be subjected to a membrane separation in a third separation zone III in order to remove at least a portion of the molecular hydrogen present therein before residual gas I is recycled into reaction zone A (this measure will be taken especially when only a comparatively small amount of hydrogen is combusted in reaction zone A). Separating membranes suitable in this context are, for example, aromatic polyamide membranes, for example those from UBE Industries Ltd. The latter include membrane types A, B-H, C and D. For such a removal, particular preference is given to the use of a UBE Industries Ltd. polyimide membrane of the B-H type. The hydrogen permutation rate for $H_2$ for this membrane at 60° C. is $0.7 \cdot 10^{-3}$ [STP·cc/$cm^2$·sec·cm Hg]. For this purpose, the $CO_2$-scrubbed residual gas I can be passed through the membrane which generally has a tubular shape (but a plate or wound module are also possible) and which is permeable only to the molecular hydrogen. The molecular hydrogen removed in this way may be used further in other chemical synetheses or, for example, sent to incineration together with residual gas I discharged in the process according to the invention. It is also possible to include the $CO_2$ released (which can also simply be discharged into the atmosphere) and also the aqueous condensates formed in separation zones I and II in this incineration.

In addition, the high boilers removed in separation zone I may be sent to the aforementioned incineration. Typically, the incineration is effected with supply of air. The incineration can be performed, for example, as described in EP-A 925 272.

The membrane removal of molecular hydrogen is preferably likewise carried out under high pressure (for example from 5 to 50 bar, typically from 10 to 15 bar).

It is therefore appropriate in accordance with the invention to carry it out immediately before the $CO_2$ scrubbing or immediately after the $CO_2$ scrubbing (preferred) of the residual gas I in order to advantageously twice utilize the pressure level increased once. In addition to plate membranes, wound membranes or capillary membranes, pipe membranes (hollow fiber membranes) in particular are also useful for the hydrogen removal. Their internal diameter may, for example, be from a few μm to a few mm. For this purpose, analogously to the tubes of a tube bundle reactor, for example, a bundle of such pipe membranes is cast into one plate in each case at both pipe ends. Outside the pipe membrane, there is preferably reduced pressure (<1 bar). The residual gas I under elevated pressure (>1 bar) is conducted toward one of the two plate ends and forced through the pipe interior to the pipe outlet present at the opposite end. Along the flow path thus defined in the tube interior, molecular hydrogen is released outward through the $H_2$-permeable membrane.

Otherwise, the residual gas I aftertreated as described (sum of aftertreated portion and any non-aftertreated portion) can be recycled as required into reaction zone A as one of the at least two feed streams comprising gaseous propane. Preferably in accordance with the invention, the entirety of residual gas I aftertreated in accordance with the invention is fed to reaction gas A starting mixture (to the charge gas mixture of reaction zone A).

Preference is given in accordance with the invention to an inventive procedure in which the highest working pressure level is present in the process step of the $CO_2$ scrubbing of residual gas I. As described, this enables the process according to the invention to be carried out with use of only one compressor (preferably of a multistage radial compressor) which is to be positioned between formation of residual gas I and $CO_2$ scrubbing of residual gas I. Especially between reaction zone A and reaction zone B, there is, as shown, not necessarily any need to use a further compressor in the process according to the invention. However, it will be appreciated that such a further compressor may be integrated into the process according to the invention.

A further advantage of the process according to the invention is that it enables the realization of minimum circulation streams. In addition, it opens up the possibility that the reaction gas A starting mixture fed to reaction zone A naturally comprises molecular hydrogen which protects the hydrocarbon present in this starting mixture from combustion with molecular oxygen present simultaneously in this mixture. Based on fresh propane converted, this results in comparatively high target product selectivities. Finally, it should be emphasized once again that a basic principle of the process according to the invention is that non-inert secondary components which are formed in the course of the process according to the invention or are introduced into it have their outlet naturally in the condensates formed in separation zones I and II of the process according to the invention.

Typically, cycle gas I recycled into reaction zone A comprises:

| | |
|---|---|
| from 50 to 90% by vol. of | propane, |
| from >0 to 5, usually to ≦2 or ≦1% by vol. of | CO, |
| from 1 to 20% by vol. of | $H_2$, |
| from 1 to 20% by vol. of | $CO_2$, |
| from 1 to 20% by vol. of | $H_2O$, |

| from 0 to 10, frequently to 5% by vol. of | $O_2$ and |
| from 0 (frequently from $\geq$0.1) to 5% by vol. of | propylene. |

Finally, it should also be emphasized that polymerization inhibitors are always added when condensed phases occur, both in separation zone I and in separation zone II. Useful such polymerization inhibitors are in principle all known process inhibitors. Particularly suitable in accordance with the invention are, for example, phenothiazine and the methyl ether of hydroquinone. Presence of molecular oxygen increases the effectiveness of the polymerization inhibitors. Acrolein obtained by the process according to the invention can be converted to the acrolein reaction products mentioned in the documents U.S. Pat. No. 6,166,263 and U.S. Pat. No. 6,187,963. Examples of acrolein reaction products are 1,3-propanediol, methionine, glutaraldehyde and 3-picoline.

EXAMPLES AND COMPARATIVE EXAMPLES

I. Long-Term Operation of a Heterogeneously Catalyzed Two-Stage Partial Oxidation of Propylene to Acrylic Acid in the Absence and in the Presence of Molecular Hydrogen A) General Experimental Setup of the Reaction Apparatus Reactor for the First Oxidation Stage The reactor consisted of a jacketed cylinder of stainless steel (cylindrical guide tube surrounded by a cylindrical outer vessel). The wall thicknesses were always from 2 to 5 mm.

The internal diameter of the outer cylinder was 91 mm. The internal diameter of the guide tube was approx. 60 mm.

At the top and bottom, the jacketed cylinder was concluded by a lid and base respectively.

The contact tube (total length 400 cm, internal diameter 26 mm, external diameter 30 mm, wall thickness 2 mm, stainless steel) was accommodated in the guide tube of the cylindrical vessel such that it just protruded in each case through the lid and base at the upper and lower end thereof (in a sealed manner). The heat exchange medium (salt melt consisting of 53% by weight of potassium nitrate, 40% by weight of sodium nitrate and 7% by weight of sodium nitrate) was enclosed in the cylindrical vessel. In order to ensure very uniform thermal boundary conditions at the outer wall of the contact tube over the entire length of contact tube within the cylindrical vessel (400 cm) the heat exchange medium was pumped in circulation by means of a propeller pump.

An electrical heater attached to the outer jacket regulated the temperature of the heat exchange medium to the desired level. Otherwise, there was air cooling.

Reactor charge: Viewed over the first-stage reactor, the salt melt and the charge gas mixture of the first-stage reactor were conducted in cocurrent. The charge gas mixture entered the first-stage reactor at the bottom. It was conducted into the reaction tube with a temperature of 165° C. in each case.

The salt melt entered the cylindrical guide tube at the bottom with a temperature $T^{in}$ and left the cylindrical guide tube at the top with a temperature $T^{out}$ which was up to 2° C. above $T^{in}$.

$T^{in}$ was adjusted so as to always give rise to a propylene conversion of 97.8±0.1 mol % in single pass at the outlet of the first oxidation stage.

Catalyst Tube Charge:

(from the bottom upward) Section A: length 90 cm

Preliminary bed of steatite spheres of diameter of 4-5 mm.

Section B: length 100 cm

Catalyst charge of a homogeneous mixture of 30% by weight of steatite rings of geometry 5 mm×3 mm×2 mm (external diameter×length×internal diameter) and 70% by weight of unsupported catalyst from section C.

Section C: length 200 cm

Catalyst charge of annular (5 mm×3 mm×2 mm=external diameter×length×internal diameter) unsupported catalyst according to example 1 of DE-A 100 46 957 (stoichiometry: $[Bi_2W_2O_9 \times 2WO_3]_{0.5}$ $[Mo_{12}CO_{5.5}Fe_{2.94}Si_{1.59}K_{0.08}O_x]_1$).

Section D: length 10 cm

Downstream bed of steatite rings of geometry
7 mm×3 mm×4 mm (external diameter×length×internal diameter)

Intermediate cooling and intermediate oxygen feeding (pure $O_2$ as secondary gas)

For the purpose of intermediate cooling (indirectly by means of air), the product gas mixture leaving the first fixed bed reactor was conducted through a connecting tube (length 40 cm, internal diameter 26 mm, external diameter 30 mm, wall thickness 2 cm, stainless steel, wound around by 1 cm of insulating material) which was mounted centrally to a length of 20 cm, charged with an inert bed of steatite rings of geometry 7 mm×3 mm×4 mm (external diameter×length×internal diameter) and was flanged directly onto the first-stage catalyst tube.

The product gas mixture always entered the connecting tube at a temperature of >$T^{in}$ (first stage) and left it with a temperature above 200° C. and below 270° C.

At the end of the connecting tube, molecular oxygen at the pressure level of the product gas mixture was metered into the cooled product gas mixture. The resulting gas mixture (charge gas mixture for the second oxidation stage) was conducted directly into the second-stage catalyst tube to which the abovementioned connecting tube was likewise flanged by its other end. The amount of molecular oxygen metered in was such that the molar ratio of $O_2$ present in the resulting gas mixture to acrolein present in the resulting gas mixture was. 1.3.

Reactor for the Second Oxidation Stage

A catalyst tube fixed bed reactor was used which was of identical design to that for the first oxidation stage. Salt melt and charge gas mixture were conducted in cocurrent viewed over the reactor. The salt melt entered at the bottom, the charge gas mixture likewise. The inlet temperature $T^{in}$ of the salt melt was adjusted so as always to result in an acrolein conversion of 99.3±0.1 mol % in single pass at the outlet of the second oxidation stage. $T^{out}$ of the salt melt was always up to 2° C. above $T^{in}$.

The catalyst tube charge (from the bottom upward) was:

Section A: Length 70 cm
  Upstream bed of steatite rings of geometry
  7 mm × 3 mm × 4 mm (external
  diameter × length × internal diameter).
Section B: Length 100 cm
  Catalyst charge of a homogeneous mixture of 30% by
  weight of steatite rings of geometry
  7 mm × 3 mm × 4 mm (external
  diameter × length × internal diameter) and
  70% by weight of coated catalyst from section C.

-continued

Section C: Length 200 cm
Catalyst charge of annular (7 mm × 3 mm × 4 mm = external diameter × length × internal diameter) coated catalyst according to preparation example 5 of DE-A 10046928 (stochiometry: $Mo_{12}V_3W_{1.2}Cu_{2.4}O_x$).
Section D: Length 30 cm
Downstream bed of steatite spheres of diameter 4-5 mm.

B) Results achieved as a function of the composition of the charge gas mixture of the first oxidation stage (the propene loading was set to 150 l (STP)/l·h; the selectivity of acrylic acid formation (assessed over both reaction stages and based on converted propylene) was always ≧94 mol %).

a) The composition of the charge gas mixture for the first oxidation stage was substantially:

| | |
|---|---|
| 7% by vol. of | propylene, |
| 12% by vol. of | $O_2$, |
| 20% by vol. of | $H_2$, |
| 5% by vol. of | $H_2O$ and |
| 56% by vol. of | $N_2$. |

At the start of the reaction apparatus charged freshly with catalyst, the inlet temperatures were:

$T^{in}$ (first oxidation stage): 320° C.
$T^{in}$ (second oxidation stage): 268° C.

After an operating time of 3 months, the inlet temperatures were:

$T^{in}$ (first oxidation stage): 330° C.
$T^{in}$ (second oxidation stage): 285° C.

b) The composition of the charge gas mixture for the first oxidation stage was substantially:

| | |
|---|---|
| 7% by vol. of | propylene, |
| 12% by vol. of | $O_2$, |
| 5% by vol. of | $H_2O$ and |
| 76% by vol. of | $N_2$. |

At the start of the reaction apparatus charged freshly with catalyst, the inlet temperatures were:

$T^{in}$ (first oxidation stage): 320° C.
$T^{in}$ (second oxidation stage): 268° C.

After an operating time of 3 months, the inlet temperatures were:

$T^{in}$ (first oxidation stage): 324° C.
$T^{in}$ (second oxidation stage): 276° C.

II. Process for Preparing Acrylic Acid from Propane (a Steady Operating State is Described)

Reaction zone A consists of a shaft furnace reactor designed as a tray reactor and configured adiabatically, which has three fixed catalyst beds arranged in succession in flow direction. The particular fixed catalyst bed is a bed, arranged on a stainless steel wire mesh, of (arranged in the series mentioned in flow direction) inert material (bed height: 26 mm; steatite spheres of diameter 1.5 to 2.5 mm) and a mixture of fresh dehydrogenation catalyst and steatite spheres (diameter 1.5 to 2.5 mm) in a bed volume ratio of dehydrogenation catalyst: steatite spheres=1:3) alternatively, it is also possible at this point to use the same amount of catalyst but undiluted).

Upstream of each fixed bed is disposed a static gas mixer. The dehydrogenation catalyst is a Pt/Sn alloy which has been promoted with the elements Cs, K and La in oxidic form and which has been applied to the outer and inner surface of $ZrO_2.SiO_2$ mixed oxide extrudants (mean length (Gaussian distribution in the range from 3 to 12 mm with maximum at approx. 6 mm): 6 mm, diameter: 2 mm) in the elemental stoichiometry (mass ratio including support) of $Pt_{0.3}Sn_{0.6}La_{3.0}Cs_{0.5}K_{0.2}(ZrO_2)_{88.3}(SiO_2)_{7.1}$ (catalyst precursor preparation and activation to the active catalyst as in example 4 of DE-A 102 19 879).

The heterogeneously catalyzed partial propane dehydrogenation is carried out in straight paths in the tray reactor described. The loading on the total amount of catalyst (calculated without inert material) of all trays with propane is 1500 l (STP)/l·h.

62 473 $m^3$ (STP)/h of reaction gas A starting mixture (T=438° C., P=2.92 bar) are fed to the first catalyst bed in flow direction and have the following composition:

50 870 $m^3$ (STP)/h of cycle gas I with the following contents:

| | |
|---|---|
| acrolein | 0.01% by vol., |
| acrylic acid | 0.01% by vol., |
| propane | 63.49% by vol., |
| propylene | 0.86% by vol., |
| $H_2$ | 14.50% by vol., |
| $O_2$ | 4.72% by vol., |
| $H_2O$ | 2.05% by vol., |
| CO | 1.17% by vol., |
| $CO_2$ | 11.17% by vol. |

3091 $m^3$ (STP)/h of steam; and
8512 $m^3$ (STP)/h of crude propane.which comprises propane to an extent of >98% by volume.

Reaction gas A starting mixture is heated from 80° C. to 438° C. by indirect heat exchange with product gas A (T=581° C.; P=2.88 bar). The crude propane is evaporated by means of the aqueous condensate obtained in separation zone I (acid water (T=33° C.), indirect heat exchange). The condensate cooled in this process can be used further for acid water condensation in separation zone I (for example in a direct cooling as a coolant). The steam is available at a temperature of 152° C. and 5 bar.

The bed height of the first catalyst bed flowed through by reaction gas A starting mixture is such that reaction gas A leaves this catalyst bed with a temperature of 549° C. and a pressure of 2.91 bar with the following contents:

| | |
|---|---|
| propane | 59.0% by vol., |
| propylene | 5.94% by vol., |
| $H_2$ | 10.25% by vol., |
| $H_2O$ | 12.98% by vol., |
| $CO_2$ | 9.97% by vol., and |
| $O_2$ | 0% by vol. |

The maximum temperature in the first catalyst bed is 592° C.

The leaving amount is 63 392 $m^3$ (STP)/h. Beyond the first catalyst bed, 986 $m^3$ (STP)/h of molecular oxygen (purity >99% by volume) are metered into reaction gas A. The oxygen has been preheated to 176° C. It is constricted to a pressure of 3.20 bar, so that the resulting pressure of the resulting reaction gas A is still 2.91 bar.

The bed height of the second catalyst bed is such that reaction gas A leaves the second catalyst bed with a temperature of 566° C. and a pressure of 2.90 bar with the following contents:

| | |
|---|---|
| propane | 51.91% by vol., |
| propylene | 9.55% by vol., |
| $H_2$ | 10.88% by vol., |
| $H_2O$ | 15.38% by vol., |
| $CO_2$ | 9.57% by vol. and |
| $O_2$ | 0% by vol. |

The maximum temperature in the second catalyst bed is 595° C.

The leaving amount is 66 058 m³ (STP)/h. Upstream of the static mixer disposed upstream of the third catalyst bed, 918 m³ (STP)/h of molecular oxygen (purity >99% by volume) (T=176° C., constricted to a pressure of 3.20 bar) are metered into this reaction gas A. The resulting pressure of the resulting reaction gas A is still 2.90 bar.

The bed height of the third catalyst bed is such that reaction gas A leaves the third catalyst bed as product gas A with a temperature of 581° C. and the pressure of 2.88 bar with the following contents:

| | |
|---|---|
| propane | 47.19% by vol., |
| propylene | 12.75% by vol., |
| $H_2$ | 11.38% by vol., |
| $H_2O$ | 17.46% by vol., |
| $CO_2$ | 9.21% by vol. and |
| $O_2$ | 0% by vol. |

The maximum temperature in the third catalyst bed is 612° C.

The leaving amount is 68 522 m³ (STP)/h. Indirect heat exchange with reaction gas A starting mixture cools product gas A to a temperature of 290° C.

13 306 m³ (STP)/h of molecular oxygen (purity >99% by volume) are metered to this product gas A (T=176° C., constricted to a pressure of 3.20 bar). The resulting pressure and the resulting temperature of the charge gas mixture thus obtainable (reaction gas B starting mixture) for the first partial oxidation stage of a two-stage partial oxidation of the propylene present in product gas B to acrylic acid are 283° C. and 1.75 bar.

The first oxidation stage is a multitube reactor having two temperature zones. The reaction tubes are configured as follows: V2A steel; external diameter 30 mm, wall thickness 2 mm, internal diameter 26 mm, length: 350 cm. From the top downward, the reaction tubes are charged as follows:

Section 1: Length 50 cm
Steatite rings of geometry 7 mm × 7 mm × 4 mm (external layout × length × internal diameter) as an upstream bed.
Section 2: Length 140 cm
Catalyst charge of a homogeneous mixture of 20% by weight (alternatively 30% by weight) of steatite rings of geometry 5 mm × 3 mm × 2 mm (external diameter × length × internal diameter) and 80% by weight (alternatively 70% by weight) of unsupported catalyst from section 3.
Section 3: Length 160 cm
Catalyst charge of annular (5 mm × 3 mm × 2 mm = external diameter × length × internal diameter) unsupported catalyst according to example 1 of DE-A 100 46 957
(Stoichiometry: $[Bi_2W_2O_9 \times 2WO_3]_{0.5}[Mo_{12}Co_{5.5}Fe_{2.94}Si_{1.59}K_{0.08}O_x]_1)$.
Alternatively, it is also possible here to use one of the catalysts EUC 1 to EUC 11 from Research Disclosure No. 497012 of Aug. 29, 2005 (the unit of the specific surface areas reported there in the working examples, which are otherwise numerically correct, is not cm²/g but m²/g).

From the top downward, the first 175 cm are thermostated by means of a salt bath A pumped in countercurrent to reaction gas B. The second 175 cm are thermostated with a salt bath B pumped in countercurrent to reaction gas B.

The second oxidation stage is likewise a multitude reactor having two temperature zones. The reaction tubes are charged from the top downward as follows:

Section 1: Length 20 cm
Steatite rings of geometry 7 mm × 7 mm × 4 mm (external diameter × length × internal diameter) as a preliminary bed.
Section 2: Length 90 cm
Catalyst charge of a homogeneous mixture of 25% by weight (alternatively 30% by weight) of steatite rings of geometry 7 mm × 3 mm × 4 mm (external diameter × length × internal diameter) and 75% by weight (alternatively 70% by weight) of coated catalyst from section 4.
Section 3: Length 50 cm
Catalyst charge of a homogeneous mixture of 15% by weight (alternatively 20% by weight) of steatite rings of geometry 7 mm × 3 mm × 4 mm (external diameter × length × internal diameter) and 85% by weight (alternatively 80% by weight) of coated catalyst from section 4.
Section 4: Length 190 cm
Catalyst charge of annular (7 mm × 3 mm × 4 mm = external diameter × length × internal diameter) coated catalyst according to preparation example 5 of DE-A 100 46 928
(Stoichiometry: $Mo_{12}V_3W_{1.2}Cu_{2.4}O_x$).

From the top downward, the first 175 cm are thermostated by means of a salt bath C pumped in countercurrent to the reaction gas. The second 175 cm are thermostated by means of a salt bath D pumped in countercurrent to the reaction gas.

Between the two oxidation stages is disposed a tube bundle heat exchanger cooled by means of salt bath, with which the product gas of the first oxidation stage can be cooled. Upstream of the entry into the second oxidation stage is disposed a valve for the supply of molecular oxygen (purity >99% by volume).

The propylene loading on the catalyst charge of the first oxidation stage is selected to be 145 l(STP)/l·h. The salt melts (53% by weight of $KNO_3$, 40% by weight of $NaNO_2$, 7% by weight of $NaNO_3$) have the following inlet temperatures:

| | |
|---|---|
| $T_A = 324°$ C. | $T_B = 328°$ C. |
| $T_C = 265°$ C. | $T_D = 269°$ C. |

Sufficient molecular oxygen (176° C., 3.20 bar) is metered to the product gas mixture of the first oxidation stage that the molar $O_2$: acrolein ratio in the resulting charge gas mixture for the second oxidation stage is 1.25. The acrolein loading on the catalyst charge of the second oxidation stage is 140 l (STP)/l·h. The pressure at the inlets to the second oxidation stage is 1.61 bar. The reaction gas leaves the intermediate cooler with a temperature of 260° C. and the inlet temperature of the charge gas mixture into the second oxidation stage is 258° C. The product gas mixture of the first oxidation stage has the following contents:

| | |
|---|---|
| acrolein | 9.02% by vol., |
| acrylic acid | 0.61% by vol., |
| propane | 39.5% by vol., |
| propylene | 0.53% by vol., |
| $H_2$ | 9.49% by vol., |
| $O_2$ | 3.90% by vol., |
| $H_2O$ | 25.75% by vol. and |
| $CO_2$ | 8.77% by vol. |

Before entry into the aftercooler, the temperature of the product gas of the first oxidation stage is 335° C.

The product gas mixture of the second oxidation stage (product gas B) has a temperature of 270° C. and a pressure of 1.55 bar, and also the following contents:

| | |
|---|---|
| acrolein | 0.049% by vol., |
| acrylic acid | 9.12% by vol., |
| acetic acid | 0.26% by vol., |
| propane | 39.43% by vol., |
| propylene | 0.53% by vol., |
| $H_2$ | 9.52% by vol., |
| $O_2$ | 2.94% by vol., |
| $H_2O$ | 26.10% by vol., |
| CO | 0.72% by vol. and |
| $CO_2$ | 9.3% by vol. |

As described in WO 2004/035514, the product gas B is fractionally condensed in a tray column (separation zone I).

As the first fuel, 118 kg/h of high boilers (polyacrylic acids (Michael adducts), etc.) are fed to the residue incineration.

From the second collecting tray above the feed of product gas B into the tray column, 23 577 kg/h of a condensed crude acrylic acid are withdrawn which has a temperature of 15° C. and 96.99% by weight of acrylic acid. As described in WO 2004/035514, this is suspension-crystallized after addition of a small amount of water, the suspension crystals are separated from the mother liquor in hydraulic wash columns and the mother liquor is recycled into the condensation column as described in WO 2004/035514. The purity of the washed suspension crystals is >99.87% by weight of acrylic acid and is suitable immediately for preparing water—"superabsorbing" polymers for use in the hygiene sector.

The amount of acid water condensate withdrawn from the third collecting tray above the feed of product gas B into the condensation column but not recycled into the condensation column is 18 145 kg/h, has a temperature of 33° C. and has the following contents:

| |
|---|
| 0.11% by weight of acrolein, |
| 1.30% by weight of acrylic acid, |
| 0.95% by weight of acetic acid and |
| 95.6% by weight of water. |

At the top of the condensation column, 53 379 m³ (STP)/h of residual gas I leave separation zone I with a temperature of 33° C. and a pressure of 1.20 bar and the following contents:

| | |
|---|---|
| acrolein | 0.03% by vol., |
| acrylic acid | 0.02% by vol., |
| propane | 61.07% by vol., |
| propylene | 0.82% by vol., |
| $H_2$ | 14.02% by vol., |
| $O_2$ | 4.55% by vol., |
| $H_2O$ | 2.00% by vol., |
| CO | 1.13% by vol. and |
| $CO_2$ | 14.36% by vol. |

0.084% by volume of residual gas I are discharged with the composition of residual gas I (as the third fuel).

The remaining amount of residual gas I (for linguistic simplification, still referred to below as "residual gas I") is compressed from 1.20 bar to 3.20 bar in the first compressor stage of a multistage radial compressor, the temperature of residual gas I rises to 92° C. Residual gas I is then divided into two halves of identical composition. One half directly forms a portion of the cycle gas I recycled into reaction zone A. The other half of residual gas I is compressed from 3.20 bar to 5.80 bar in a second compressor stage. This heats it to 127° C. In an indirect heat exchanger, it is cooled to 78° C. without any condensate forming (coolant is $CO_2$-scrubbed residual gas I of temperature 42° C. and of pressure 4.25 bar which has been depleted of molecular hydrogen by means of subsequent membrane removal and subsequently decompressed in an expansion turbine). By means of indirect air cooling, residual gas I is cooled from 78° C. to 54° C. without condensate formation. In a further compressor stage, residual gas I is compressed from 5.80 bar to 12.0 bar, in the course of which it is heated from 54° C. to 75° C.

The residual gas I thus compressed is conducted into the lower section of a column with random packing (separation zone II). At the top of this scrubbing column, 18 000 kg/h of an aqueous $K_2CO_3$ solution which has a temperature of 82° C. and comprises phenothiazine as a polymerization inhibitor are introduced. At the top of the scrubbing column, $CO_2$-scrubbed residual gas I escapes, which has the following contents at a pressure of 12.00 bar and a temperature of 85° C.:

| | |
|---|---|
| propane | 65.94% by vol., |
| propylene | 0.89% by vol., |
| $H_2$ | 15.13% by vol., |
| $O_2$ | 4.91% by vol., |
| $H_2O$ | 2.16% by vol., |
| CO | 1.22% by vol. and |
| $CO_2$ | 7.75% by vol.. |

The $CO_2$-scrubbed residual gas I (24 528 m³ (STP)/h) is conducted to a bundle of cast pipe membranes (external pressure 0.1 bar; polyimide membrane of the B-H type from UBE Industries Ltd.) and leaves it (p=12.00 bar; T=85° C.) with the following contents:

| | |
|---|---|
| propane | 66.1% by vol., |
| propylene | 0.89% by vol., |
| $H_2$ | 15.03% by vol., |
| $O_2$ | 4.92% by vol., |

-continued

| | |
|---|---|
| H₂O | 2.10% by vol., |
| CO | 1.22% by vol. and |
| CO₂ | 7.73% by vol. |

In a multistage expansion turbine, residual gas I (24 461 m³ (STP)/h) is then decompressed from 12.00 bar to 4.25 bar and cooled from 85° C. to 42° C. In indirect heat exchange with residual gas I which comes from separation zone I and has been compressed in a first stage, the CO₂-scrubbed and H₂ depleted residual gas I is heated from 42° C. to 97° C. and is recycled as cycle gas I into reaction gas A starting mixture for reaction zone A together with the other half of the remaining (non-CO₂-scrubbed) residual gas I from the fractional condensation of product gas B.

The permeate stream (67.2 m³ (STP)/h) has the following contents:

| | |
|---|---|
| propane | 0.12% by vol., |
| propylene | 0.01% by vol., |
| H₂ | 56.2% by vol., |
| H₂O | 27.2% by vol., |
| CO | 0.15% by vol. and |
| CO₂ | 12.39% by vol. |

It is sent as the fourth fuel to the combined incineration plant.

21 846 kg/h of aqueous potassium hydrogencarbonate solution are withdrawn from the bottom of the CO₂ scrubbing column and, heated from 75° C. to 100° C. by indirect heat exchange (the heat carrier used is dissociated potassium hydrogencarbonate solution), introduced to the top of a second column with random packing (dissociation column). In countercurrent, 26 m³ (STP)/h of steam (144° C., 4 bar) are conducted into the lower section of the dissociation column. The gas stream escaping at the top of the column is subjected to direct cooling (coolant: condensate formed beforehand) and the aqueous condensate which forms is introduced to the column as reflux. The escaping CO₂ is sent to the combined incineration plant as the fifth fuel. 14 968 kg/h of water are evaporated off from the effluent of the dissociation column (32 968 kg/h). The remaining amount is (postneutralized with KOH if appropriate) recycled as scrubbing solution to the top of the CO₂ scrubbing column.

Fuels 1 to 5 are incinerated together in an incineration plant with addition of air (17 674 m³ (STP)/h).

What is claimed is:

1. A process for preparing acrolein, or acrylic acid or a mixture thereof from propane, in which
   A) at least two gaseous feed streams comprising propane, at least one of which comprises fresh propane, are fed to a first reaction zone A to form a reaction gas A,
      in reaction zone A, reaction gas A is conducted through at least one catalyst bed in which partial heterogeneously catalyzed dehydrogenation of the propane forms molecular hydrogen and propylene,
      molecular oxygen which oxidizes molecular hydrogen present in reaction gas A in reaction zone A to steam is fed to reaction zone A, and
      product gas A which comprises molecular hydrogen, steam, propylene and propane is withdrawn from reaction zone A,
   B) in a reaction zone B, the product gas A withdrawn from reaction zone A, with feeding of molecular oxygen, is used to charge at least one oxidation reactor with a reaction gas B comprising molecular hydrogen, steam, propane, propylene and molecular oxygen, and the propylene present therein is subjected to a heterogeneously catalyzed partial gas phase oxidation to give a product gas B comprising acrolein, or acrylic acid or a mixture thereof as a target product, unconverted propane, molecular hydrogen, steam, carbon dioxide as a by-product, and also other secondary components having lower and higher boiling points than water,
   C) product gas B is conducted out of reaction zone B, and target product, water and secondary components having a higher boiling point than water present therein are removed therefrom in a first separation zone I to leave a residual gas I which comprises unconverted propane, carbon dioxide, molecular hydrogen, secondary components having a lower boiling point than water and any propylene unconverted in reaction zone B and any unconverted molecular oxygen,
   D) as an aftertreatment measure 1, carbon dioxide present in residual gas I is scrubbed out and any water still present in residual gas I is optionally condensed out in a second separation zone II,
      as an aftertreatment measure 2, a portion of residual gas I is discharged,
      optionally, as an aftertreatment measure 3, molecular hydrogen present in residual gas I is removed by means of a separating membrane in a third separation zone III and
      optionally, as an aftertreatment measure 4, any molecular oxygen present in residual gas I is reduced chemically,
   the sequence of use of aftertreatment measures 1 to 4 being as desired, and
   E) aftertreated residual gas I which comprises unconverted propane and remains after use of aftertreatment measures 1 and 2 and, optionally 3 and/or 4 is recycled into reaction zone A as at least one of the two feed streams comprising propane,
      wherein
      an amount M of molecular hydrogen which is at least 5 mol % but not more than 95 mol % of the total amount of molecular hydrogen produced in reaction zone A and, optionally, fed to reaction zone A is oxidized to steam in reaction zone A.

2. The process according to claim 1, wherein an amount M of molecular hydrogen which is at least 10 mol % but not more than 90 mol % of the total amount of molecular hydrogen produced in reaction zone A and, optionally, fed to reaction zone A is oxidized to steam in reaction zone A.

3. The process according to claim 1, wherein an amount M of molecular hydrogen which is at least 20 mol % but not more than 80 mol % of the total amount of molecular hydrogen produced in reaction zone A and, optionally, fed to reaction zone A is oxidized to steam in reaction zone A.

4. The process according to claim 1, wherein an amount M of molecular hydrogen which is at least 40 mol % but not more than 60 mol % of the total amount of molecular hydrogen produced in reaction zone A and, optionally, fed to reaction zone A is oxidized to steam in reaction zone A.

5. The process according to any of claims 1 to 4, wherein the reaction gas B with which the at least one oxidation reactor is charged has the following contents:
   from 4 to 25% by volume of propylene,
   from 6 to 70% by volume of propane,
   from 5 to 60% by volume of H₂O, from 8 to 65% by volume of $O_2$ and
from 0.3 to 20% by volume of $H_2$.

6. The process according to any of claims 1 to 4, wherein the reaction gas B with which the at least one oxidation reactor is charged has the following contents:
from 6 to 15% by volume of propylene,
from 6 to 60% by volume of propane,
from 5 to 30% by volume of $H_2O$,
from 8 to 35% by volume of $O_2$ and
from 2 to 18% by volume of $H_2$.

7. The process according to claim 5, wherein the molar ratio V1 of propane present in reaction gas B to propylene present in reaction gas B is from 1 to 9.

8. The process according to claim 5, wherein the molar ratio V1 of propane present in reaction gas B to propylene present in reaction gas B is from 1 to 7.

9. The process according to any of claims 1 to 4, wherein the source used for the molecular oxygen required in reaction zone B is pure molecular oxygen or a mixture of molecular oxygen and inert gas which comprises not more than 10% by volume of inert gas.

10. The process according to any of claims 1 to 4, wherein the source used for the molecular oxygen required in reaction zone A is pure molecular oxygen or a mixture of molecular oxygen and inert gas which comprises not more than 10% by volume of inert gas.

11. The process according to any of claims 1 to 4, wherein the source used for molecular oxygen required in reaction zone A is air and the source used for molecular oxygen required in reaction zone B is pure molecular oxygen or a mixture of molecular oxygen and inert gas which comprises not more than 10% by volume of inert gas.

12. The process according to any of claims 1 to 4, wherein the reaction gas B with which the at least one oxidation reactor is charged comprises from 0.1 to 30% by volume of $CO_2$.

13. The process according to any of claims 1 to 4, wherein the reaction gas B with which the at least one oxidation reactor is charged comprises from 1 to 20% by volume of $CO_2$.

14. The process according to any of claims 1 to 4, wherein the reaction gas B with which the at least one oxidation reactor is charged comprises $\leq$5% by volume of molecular nitrogen.

15. The process according to any of claims 1 to 4, wherein reaction zone A is configured adiabatically.

16. The process according to any of claims 1 to 4, wherein reaction zone A is designed as a tray reactor.

17. The process according to any of claims 1 to 4, wherein the aftertreated residual gas I recycled into reaction zone A comprises molecular oxygen, steam, molecular hydrogen, CO and $CO_2$.

18. The process according to any of claims 1 to 4, wherein the aftertreated residual gas I recycled into reaction zone A comprises from 5 to 15% by volume of $CO_2$.

19. The process according to any of claims 1 to 4, wherein $CO_2$ is scrubbed out of residual gas I by means of an aqueous solution comprising potassium carbonate.

20. The process according to any of claims 1 to 4, wherein the scrubbing of $CO_2$ out of residual gas I is carried out at a pressure of from 3 to 50 bar.

21. The process according to any of claims 1 to 4, wherein an amount of water which is at least 70 mol % of the amount of water formed in reaction zone B is removed from product gas B in separating zone I.

22. The process according to any of claims 1 to 4, wherein an amount of water which is at least 90 mol % of the amount of water formed in reaction zone B is removed from product gas B in separating zone I.

23. The process according to any of claims 1 to 4, wherein the amount of propane present in the discharged residual gas I per unit time is less than 30 mol % based on the amount of fresh propane fed into the process per unit time.

24. The process according to any of claims 1 to 4, wherein the amount of propane recycled into reaction zone A in aftertreated residual gas I is at least 90 mol % of the amount of propane present in product gas B.

* * * * *